US011597845B2

(12) United States Patent
Roper, III et al.

(10) Patent No.: US 11,597,845 B2
(45) Date of Patent: Mar. 7, 2023

(54) COATING FOR ALDEHYDE REMEDIATION AND METHOD OF MAKING

(71) Applicants: Dow Global Technologies LLC; Rohm and Haas Company, Collegeville, PA (US); Georgia Tech Research Corporation, Atlanta, GA (US); Georgia State University Research Foundation, Inc., Atlanta, GA (US)

(72) Inventors: John Anderson Roper, III, Midland, MI (US); Sudhakar Balijepalli, Midland, MI (US); Paul Doll, North Wales, PA (US); Andreas S. Bommarius, Atlanta, GA (US); Christopher W. Jones, Mableton, GA (US); Christopher R. Murdock, Atlanta, GA (US); John M. Robbins, Atlanta, GA (US); Akihiro Nomura, Atlanta, GA (US); Bettina R. Bommarius, Atlanta, GA (US); Adam Holewinski, Boulder, CO (US); Giovanni Gadda, Atlanta, GA (US)

(73) Assignees: DOW GLOBAL TECHNOLOGIES LLC, Midland, MI (US); ROHM AND HAAS COMPANY, Collegeville, PA (US); GEORGIA TECH RESEARCH CORPORATION, Atlanta, GA (US); GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 397 days.

(21) Appl. No.: 16/625,881

(22) PCT Filed: Jun. 29, 2018

(86) PCT No.: PCT/US2018/040229
§ 371 (c)(1),
(2) Date: Dec. 23, 2019

(87) PCT Pub. No.: WO2019/006263
PCT Pub. Date: Jan. 3, 2019

(65) Prior Publication Data
US 2020/0165463 A1 May 28, 2020

Related U.S. Application Data

(60) Provisional application No. 62/527,481, filed on Jun. 30, 2017.

(51) Int. Cl.
C09D 5/02 (2006.01)
C09D 7/40 (2018.01)
C09D 7/48 (2018.01)
C12N 11/14 (2006.01)
C09D 189/00 (2006.01)

(52) U.S. Cl.
CPC ............... *C09D 5/024* (2013.01); *C09D 7/48* (2018.01); *C09D 7/68* (2018.01); *C09D 7/69* (2018.01); *C09D 7/70* (2018.01); *C09D 189/00* (2013.01); *C12N 11/14* (2013.01); *C12Y 102/03001* (2013.01)

(58) Field of Classification Search
CPC ...... C09D 189/00; C09D 5/022; C09D 5/024; C09D 7/48; C09D 7/68; C09D 7/69; C09D 7/70; C09D 7/61; C09D 7/65; C12N 11/14; C12Y 102/03001; C08K 3/36
See application file for complete search history.

(56) References Cited

U.S. PATENT DOCUMENTS

| | | | |
|---|---|---|---|
| 3,985,616 A | 10/1976 | Weaver et al. | |
| 4,003,865 A | 1/1977 | Nowak et al. | |
| 4,371,612 A | 2/1983 | Matsumoto et al. | |
| 4,547,350 A | 10/1985 | Gesser | |
| 4,727,030 A | 2/1988 | Ishimura et al. | |
| 4,892,719 A | 1/1990 | Gesser | |
| 4,978,619 A | 12/1990 | Kajiwara et al. | |
| 4,994,385 A | 2/1991 | Bienarz et al. | |
| 5,482,996 A | 1/1996 | Russell et al. | |
| 5,643,721 A | 7/1997 | Spring et al. | |
| 5,914,367 A | 6/1999 | Dordick et al. | |
| 6,997,980 B2 | 2/2006 | Wegner et al. | |
| 7,132,247 B1 | 11/2006 | Lyngberg et al. | |
| 7,923,513 B2 | 4/2011 | Killilea et al. | |
| 2009/0226651 A1 | 9/2009 | Chisholm et al. | |
| 2009/0238811 A1 | 9/2009 | McDaniel et al. | |
| 2009/0022644 A1 | 12/2009 | Sweredjuk | |
| 2010/0291632 A1* | 11/2010 | Zuffi | C07D 473/40 435/88 |
| 2011/0250626 A1 | 10/2011 | Williams et al. | |
| 2012/0028333 A1 | 2/2012 | Piatesi et al. | |
| 2012/0097194 A1 | 4/2012 | McDaniel et al. | |
| 2012/0245267 A1 | 9/2012 | Blanchard et al. | |
| 2015/0191607 A1* | 7/2015 | McDaniel | C09D 5/1625 424/94.64 |
| 2015/0328490 A1* | 11/2015 | McDaniel | C09D 5/34 106/18.32 |

FOREIGN PATENT DOCUMENTS

CN 101366137 A 2/2009
CN 101914516 B 12/2012
(Continued)

OTHER PUBLICATIONS

Nomura et al. Ind. Eng. Chem. Res. (2015; published online Dec. 15, 2014) 54: 263-271 (Year: 2014).*

(Continued)

*Primary Examiner* — Susan M Hanley
(74) *Attorney, Agent, or Firm* — Cantor Colburn LLP

(57) ABSTRACT

A coating for conversion of formaldehyde to carbon dioxide includes an alcohol/aldehyde oxidase and a formate oxidase immobilized on a solid particulate support; and a latex binder.

16 Claims, 2 Drawing Sheets

Specification includes a Sequence Listing.

(56) References Cited

FOREIGN PATENT DOCUMENTS

| CN | 105038559 A | 11/2015 | |
|---|---|---|---|
| CN | 105964133 A | 9/2016 | |
| GB | 232723 A | 4/1925 | |
| JP | 2000144016 A | 5/2000 | |
| JP | 2005126561 A | 5/2005 | |
| JP | 20050131567 A | 5/2005 | |
| WO | WO-9936516 A2 * | 7/1999 | ............... A01H 1/04 |
| WO | WO-2005073257 A1 * | 8/2005 | ............... C08F 2/22 |
| WO | 2009133990 A1 | 11/2009 | |
| WO | WO-2012129555 A2 * | 9/2012 | ............... C12N 1/38 |

OTHER PUBLICATIONS

English translation of of Morikawa et al. Technical Report of Aichi Industrial Technology Institute (2007), 6:126-127 (Year: 2007).*

Morikawa et al. Aichi-ken Sangyo Gijutsu Kenkyusho Kenkyu Hokoku (Technical Report of Aichi Industrial Technology Institute (2007), 6:126-127 in the original Japanese (Year: 2007).*

ASTM D2244-05; "Standard Practice for Calculation of Color Tolerances and Color Differences from Instrumentally Measured Color Coordinates"; ASTM International; 2005; 10 pages.

Blum et al.; "Improved thermostability of amino ester hydrolase (AEH) by combining B-FIT analysis and structure-guided consensus method"; Journal of Biotechnology, vol. 160; 2012; pp. 214-221.

Bradford, Marion M. "A Rapid and Sensitive Method for the Quantitation of Microgram Quantities of Protein Utilizing the Principle of Protein-Dye Binding", Analytical Biochemistry, (1976), vol. 72, pp. 248-254.

Chaikittisilp et al; "Poly(Allylamine)-Mesaporous Silica Composite Materials for CO2 Capture from Simulated Flue Gas or Ambient Air"; Industrial & Engineering Chemistry Research, vol. 50; Nov. 17, 2011; pp. 14203-14210.

Cregg et al.; "Functional Characterization of the Two Alcohol Oxidase Genes from the Yeast *Pichia pastoris*"; Molecular and Cellular Biology, vol. 9, Issue No. 3; Mar. 1989; pp. 1316-1323.

Database geneseq; [Online ]: Oct. 8, 1999 (Oct. 8, 1999); "Pichia pastoris alcohol Oxidase ZZA1"; retrieved from EBI accession No. GSP AAY03576.

Datta et al.; "DNA template-assisted modulation of horseradish peroxidase activity"; International Journal of Biological Macromolecules, vol. 50; 2012; pp. 552-555.

Demicheva; "Novel Oxygen Scavenger Systems for Functional Coatings"; Degree Thesis; Arcada, Evonik Industries AG; 2015; pp. 1-56.

Drese et al.; "Aminosilica Materials as Adsorbents for the Selective Removal of Aldehydes and Ketones from i —I Simulated Bio-oil."; ChemSusChem, vol. 4; 2011; pp. 379-385.

Edmondson; "Intramolecular hemiacetal formation in 8-formylriboflavine"; Biochemistry, vol. 13, Issue No. 14; Jul. 1974; pp. 2817-2821.

Eggeling et al.; "Direct Enzymatic Assay for Alcohol Oxidase, Alcohol Dehydrogenase, and Formaldehyde Dehydrogenase in Colonies of Hansenula polymorpha", Applied and Environmental Microbiology, vol. 39, Issue No. 1; 1980; pp. 268-269.

Fang et al.; "Magnetic Bio/Nanoreactor wth Multilayer Shells of Glucose Oxidase and Inorganic Nanoparticles"; Langmuir, vol. 18, Issue No. 16; May 29, 2002; pp. 6338-6344.

Finnegan et al.; "Role of valine 464 in the flavin oxidation reaction catalyzed by choline oxidase", Biochemistry, vol. 49; Feb. 25, 2010; pp. 2952-2961.

Finnegan et al.; "Structural and kinetic studies on the Sort101Ala variant of choline oxidase: catalysis by compromise", Archives of Biochemistry and Biophysics, vol. 501; 2010; pp. 207-213.

Flickinger et al.; "Painting and Printing Living Bacteria: Engineering Nanoporous Biocatalytic Coatings to Preserve Microbial Viability and Intensify Reactivity"; Biotechnology Prog., vol. 23; Jan. 5, 2007; pp. 2-17.

Gill et al.; "Magnetic Nanoparticie Polymer Brush Catalysts: Alternative Hybrid Organic/Inorganic Structures to Obtain High, Local, Catalyst Loadings for Use in Organic Transformations"; Catalysis Letters, vol. 131; 2009; pp. 425-431.

Gosse et al.; "A versatile method for preparation of hydrated microbial-latex biocataiytic coatings for gas absorption and and gas evolution"; Journal of Industrial Microbiology and Biotechnology, vol. 39; May 17, 2012; pp. 1269-1278.

Gray et al.; "Rapid Evolution of Reversible Denaturation and Elevated Melting Temperature in a Microbial Haloalkane Dehalogenase"; Advanced Synthesis and Catalysis, vol. 343, Issue No. 6-7; 2001; pp. 607-617.

Gvozdev et al.; "Purification and Properties of Alcohol Oxidase from Pichia putida"; Biochemistry, vol. 75, Issue No. 2; 2010; pp. 242-248.

Hayashi et al.; "Competitive oxidation of 1- and 2-propanol catalyzed by titanium silicate-1 and the application of selective oxidation of 1-methoxy-2-propanol to 1-methoxy-2-propanone"; Catalysis Letters, vol. 36; 1996; pp. 99-102.

Hicks et al.; "Designing Adsorbents for CO2 Capture From Flue Gas—Hyperbranched Aminosilicas Capable of Capturing CO2 Reversibly."; Journal of the American Chemical Society, vol. 130; Feb. 19, 2008; pp. 2902-2903.

Hicks et al.; "Spacing and Site Isolation of Amine Groups in 3-Aminopropyl-Grafted Silica Materials: the Role of Protecting Groups."; Chemistry of Materials, vol. 18, Issue 21; Sep. 22, 2006; pp. 5022-5032.

ISR/WO, dated Sep. 28, 2018.

Johansson et al.; "Oxygen scavenging enzymes in coatings—effect of coating procedures on enzyme activity"; Nordic Pulp and Paper Research Journal, vol. 28; Jan. 2011; pp. 197-204.

Johansson; "Oxygen-reducing enzymes in coatings and films for active packaging"; Karlstads University; Dissertation; 2013; pp. 1-106.

Kato et al: "Formaldehyde dismutase, a novel NAD-binding oxidoreductase from Pseudomonas putida F61"; European Journal of Biochemistry, vol. 156; 1986; pp. 59-64.

Kotsira et al; "Oxalate oxidase from barley roots: purification to homogeneity and study of some molecular, catalytic, and binding properties". Archives of Biochemistry and Biophysics, vol. 340, Issue No. 2; Apr. 15, 1997; pp. 239-249.

Maeda et al.; "Expression in *Escherichia coli* of an Unnamed Protein Gene from Aspergillus oryzae RIB40 Cofactor Analyses of the Gene Product as Formate Oxidase"; Bioscience Biotechnology and Biochemistry, vol. 73, Issue No. 12; Dec. 7, 2009; pp. 2645-2649.

Moomaw et al.; "Metal dependence of oxalate decarboxylase activity", Biochemistry, vol. 48, Issue No. 26; May 27, 2009; pp. 6116-6125.

Nomura et al.; "Enhanced Formaldehyde-Vapor Adsorption Capacity of Polymeric Amine-Incorporated Aminosilicas"; Chem. Eur. J., vol. 20; Apr. 3, 2014; pp. 6381-6390.

Ozimek et al.; "Alcohol oxidase: A complex peroxisomal, oligomeric flavoprotein" FEMS Yeast Research, vol. 5; Aug. 24, 2005; pp. 975-983.

Payne et al.; "High-level production of spinach glycolate oxidase in the methylotrophic yeast *Pichia pastoris*: Engineering a biocatalyst"; Gene, vol. 167; 1995; pp. 215-219.

Payne; "A New Epoxy Aldehyde: Synthesis of Glycidaldehyde from Acrolein and Hydrogen Peroxide", Journal of the American Chemical Society, vol. 80, Issue No. 23; 1958; p. 6461.

Qian et al.; "Investigating the Structural and Functional Consequences of Circular Permutation on Lipase B from Candida Antarctica"; ChemBioChem vol. 8, Issue No. 16; Sep. 17, 2007; pp. 1989-1996.

Qian et al.; "Structural redesign of lipase B from candida antarctica by circular permutation and incremental truncation"; Journal of Molecular Biology, vol. 393, Issue No. 1; 2009; pp. 191-201.

Quaye et al.; "Role of Glu312 in Binding and Positioning of the Substrate for the Hydride Transfer Reaction in Choline Oxidase"; Biochemistry, vol. 47, Dec. 12, 2007; pp. 243-256.

(56) References Cited

OTHER PUBLICATIONS

Salach et al.; "Studies on Succinate Dehydrogenase: Site of Attachment of the Covalently-Bound Flavin to the Peptide Chain"; European Journal of Biochemistry, vol. 26, Issue No. 2; Mar. 1972; pp. 267-278.

Sauer et al.; "Photocatalyzed Oxidation of Ethanol and Acetaldehyde in Humidified Air"; Journal of Catalysis, vol. 158; 1996; pp. 570-582.

Test Method JC/T 1074-2008; "Purificatory Performance of Coatings with Air Purification"; 2008; 3 pages.

Tiwari et al.; "Role of Conserved Glycine in Zinc-dependent Medium Chain Dehydrogenase/Reductase Superfamily"; The Journal of Biological Chemistry, vol. 287, Issue No. 23; Jun. 1, 2012; pp. 19429-19439.

Vazquez-Figueroa et al.; "Development of a Thermostable Glucose Dehydrogenase via a Structure-guided Consensus Concept"; ChemBioChem, vol. 8; 2007; pp. 2295-2301.

Vazquez-Figueroa et al.; "Thermostable Variants Constructed via the Structure-guided Consensus Method also Show Increased Stability in Salt Solutions and Homogeneous Aqueous-Organic Media"; Protein Engineering Design and Selection, vol. 21, Issue No. 11; Sep. 16, 2008; pp. 673-680.

Winestrand et al.; "Co-immobilization of oxalate oxidase and catalase in films for scavenging of oxygen or oxalic acid"; Biochemical Engineering Journal, vol. 72; 2013; pp. 96-101.

Yanase et al.; "Cloning, Sequence Analysis, and Expression of the Gene Encoding Formaldehyde Dismutase from Pseudomonase putide F61", Bioscience Biotechnology and Biochemistry, vol. 59, Issue No. 2; 1995; pp. 197-202.

Yasahura et al.; "Production of Aldehyde Oxidases by Microorganisms and Their Enzymatic Properties"; Journal of Bioscience and Bioengineering, vol. 34, Issue No. 2; 2002: pp. 124-129.

International Search Report and Written Opinion for International Application PCT/US2018/040229; International Filing Date: Jun. 29, 2018; dated Sep. 28, 2018; 8 pages.

\* cited by examiner

COATING FOR ALDEHYDE REMEDIATION AND METHOD OF MAKING

CROSS REFERENCE TO RELATED APPLICATIONS

This application is a National Stage application of PCT/US2018/040229, filed on Jun. 29, 2018, which claims the benefit of U.S. Provisional Application No. 62/527,481, filed on Jun. 30, 2017, both of which are incorporated by reference in their entirety herein.

BACKGROUND

This invention relates to the remediation of formaldehyde, in particular the remediation of formaldehyde using a combination of immobilized enzymes.

Immobilized bioreagents, in particular immobilized enzymes, have been used for a wide variety of applications, from removing organic compounds from waste water, in biosensors, biodiesel and antibiotic production, and in the food industry. Nonetheless, identification of appropriate enzymes, immobilization of those enzymes, and determining the particular conditions in which they will function is highly unpredictable. The use of immobilized enzymes to achieve a specific purpose therefore presents an ongoing challenge in the art. For example, there are no commercially available enzyme systems for the remediation of formaldehyde. Formaldehyde can be considered an environmental contaminant, particularly in building interiors. Indoor air quality (IAQ) is an area of emerging importance due to increased awareness among consumers for the need for comfort, health, and wellness of occupants in buildings. New methods for the remediation of formaldehyde from the environment, such as in building interiors, would accordingly be highly desirable.

SUMMARY

In an aspect, a coating for conversion of formaldehyde to carbon dioxide comprises an alcohol/aldehyde oxidase (AOX) and a formate oxidase (FOX), wherein both the alcohol/aldehyde oxidase and the formate oxidase are immobilized on a solid particulate support; and a latex binder.

In another aspect, a liquid coating composition for the formation of the foregoing coating comprises an aldehyde oxidase and a formate oxidase immobilized on a solid particulate support; and a liquid latex binder composition.

In yet another aspect, a method for forming a coating comprises coating the foregoing the liquid coating composition onto a substrate; and drying the liquid coating composition to form the coating.

In a further aspect, a method for converting atmospheric formaldehyde to carbon dioxide comprises contacting the foregoing coating with an atmosphere comprising formaldehyde; and converting at least a portion of the formaldehyde to carbon dioxide.

In another aspect, an alcohol/aldehyde oxidase is of SEQ ID NO: 1 having a R241K mutation or a N218D mutation.

The above described and other features are exemplified by the following figures and detailed description.

BRIEF DESCRIPTION OF THE DRAWINGS

The following Figures are exemplary embodiments wherein the like elements are numbered alike.

DETAILED DESCRIPTION

Figure 1:
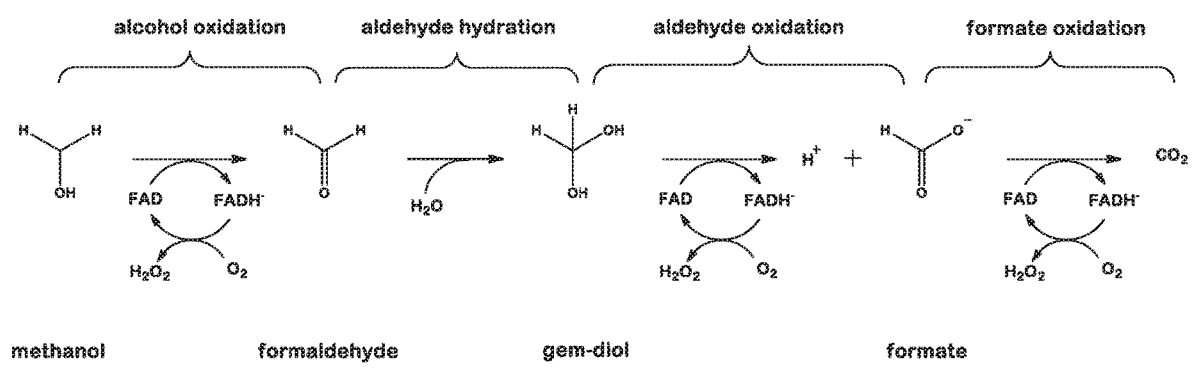
FIG. 1 is a schematic of a proposed mechanism for the enzymatic decomposition of formaldehyde.

The inventors hereof have surprisingly found that a composition comprising the enzymes alcohol/aldehyde oxidase (AOX) and formate oxidase (FOD or FOX) immobilized onto a solid particulate support and combined with a latex binder can be used to form a bioactive coating. A liquid composition comprising AOX and FOX immobilized on a solid particulate support and further containing a latex binder can be coated onto a substrate and dried to form a coating. The bioactive coating can catalyze the conversion of formaldehyde to carbon dioxide within 24 hours. A proposed mechanism for the enzymatic decomposition of formaldehyde is shown in FIG. 1.

The compositions include an alcohol/aldehyde oxidase (AOX). Alcohol oxidase from methylotrophic yeast, for example, is an octameric enzyme with subunits of 80 kD. Its function is part of the ability to oxidize alcohols such as methanol and ethanol to their acids via aldehydes and equimolar production of hydrogen peroxide via consumption of molecular oxygen. AOX is very sensitively induced by methanol and is produced in large amounts and then stored in peroxisomes. AOX is a flavin adenine dinucleotide (FAD) containing enzyme with 1 flavin adenine dinucleotide (FAD per subunit. The ability of its promoter to be induced by methanol made it an early target for heterologous yeast expression that led to the establishment of *Pichia pastoris* as a heterologous expression system.

AOXs have been isolated from *Pichia* species (now called *Komatagaella*), *Hansenula* species (now called *Ogataea*) and *Candida* species. Each has multiple strains that all have an AOX gene. Others that are not as closely related, but still have activity and can be used in the compositions and methods described herein include AOX from *Aspergillus* species, *Fusarium* species and *Colletotrichum* species with about 60-70% identity to the *Pichia pastoris* AOX.

In one aspect, the AOX is the wild-type AOX from a *Pichia* species such as *Pichia pastoris* having SEQ ID NO: 1, or a variant having greater than 70, 75, 80, 85, 90, 95, 98, or 99% homology thereto.

```
                                              (SEQ ID NO: 1)
MAIPEEFDILVLGGGSSGSCIAGRLANLDHSLKVGLIEAGENNLNNPWVY

LPGIYPRNMKLDSKTASFYTSNPSPHLNGRRAIVPCANVLGGGSSINFMM

YTRGSASDYDDFQAEGWKTKDLLPLMKKTETYQRACNNPDIHGFEGPIKV

SFGNYTYPVCQDFLRASESQGIPYVDDLEDLVTAHGAEHWLKWINRDTGR

RSDSAHAFVHSTMRNHDNLYLICNTKVDKIIVEDGRAAAVRTVPSKPLNP
```

-continued
```
KKPSHKIYRARKQIVLSCGTISSPLVLQRSGFGDPIKLRAAGVKPLVNLP

GVGRNFQDHYCFFSPYRIKPQYESFDDFVRGDAEIQKRVFDQWYANGTGP

LATNGIEAGVKIRPTPEELSQMDESFQEGYREYFEDKPDKPVMHYSIIAG

FFGDHTKIPPGKYMTMFHFLEYPFSRGSIHITSPDPYAAPDFDPGFMNDE

RDMAPMVWAYKKSRETARRMDHFAGEVTSHHPLFPYSSEARALEMDLETS

NAYGGPLNLSAGLAHGSWTQPLKKPTAKNEGHVTSNQVELHPDIEYDEED

DKAIENYIREHTETTWHCLGTCSIGPREGSKIVKWGGVLDHRSNVYGVKG

LKVGDLSVCPDNVGCNTYTTALLIGEKTATLVGEDLGYSGEALDMTVPQF

KLGTYEKTGLARF
```

In an aspect, the AOX is a novel R241K variant of SEQ ID NO: 1. In another aspect, the AOX is an N218D variant of SEQ ID NO: 1.

Figure 2:
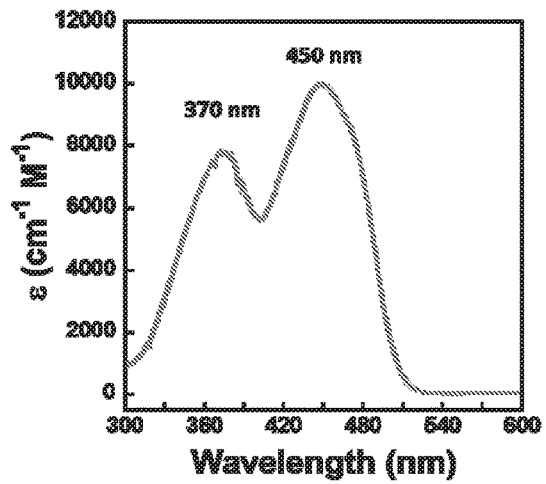
FIG. 2 shows that wild-type FOX exhibits an unusual UV absorption spectrum that was due to a non-covalently bound 8-formyl flavin adenine dinucleotide (FAD) in place of the typical FAD cofactor present in most glucose-methanol-choline (GMC) oxidoreductases.
Figure 2:
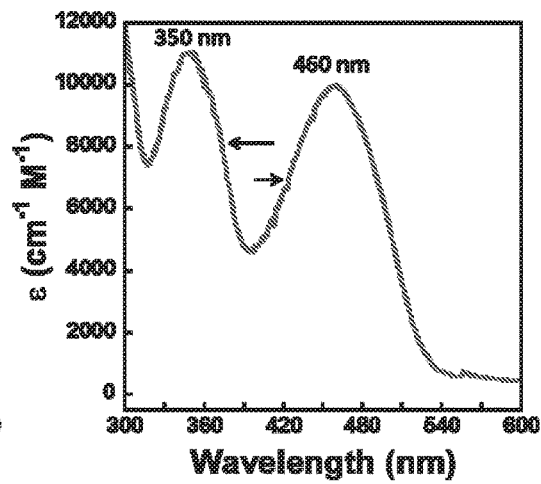

The compositions also include a formate oxidase. Formate oxidase (FOX; E.C. 1.2.3.1) from *Aspergillus oryzae* has been identified as the first and only member of the glucose-methanol-choline (GMC) oxidoreductase superfamily of enzymes to oxidize a carbonic acid. Additionally, wild-type FOX has been shown to exhibit an unusual UV absorption spectrum that was due to a non-covalently bound 8-formyl flavin adenine dinucleotide (FAD) in place of the typical FAD cofactor present in most GMC oxidoreductases. (FIG. 2)

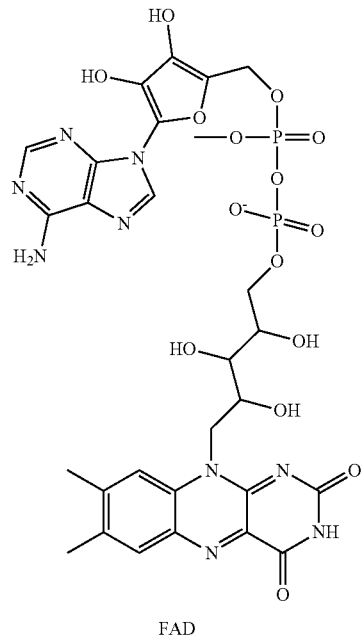

FAD

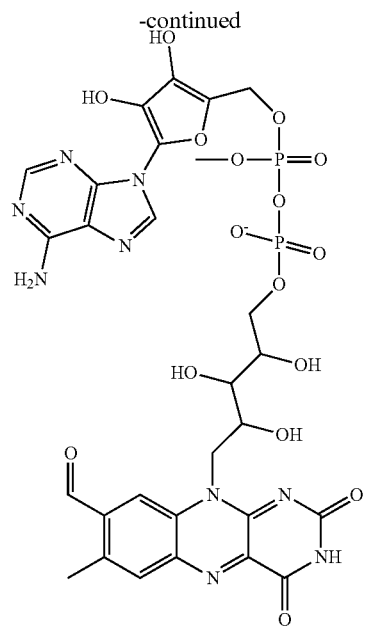

8-formyl FAD

Although the presence of an enzyme bound 8-formyl flavin mononucleotide (FMN) has been reported previously as a result of site-directed mutational studies on lactate oxidase (LOX), FOX is the first reported case of 8-formyl FAD being present in a wild-type enzyme. Since the formation of 8-formyl FMN in LOX has been shown previously to result in complete inactivation of the enzyme, the presence of 8-formyl FAD in FOX was proposed to be an artifact. Therefore, both the formation and role of the 8-formyl FAD cofactor in formate oxidase was investigated through the use of steady-state kinetics, rapid-reaction kinetics, kinetic isotope effects, site-directed mutagenesis, ICP analysis, UV and fluorescence spectrometry, LCMS, electron paramagnetic resonance (EPR) spectroscopy, analytical ultracentrifugation (AUC), and light-exposure studies. Surprisingly, the results from these studies not only indicate that 8-formyl-FAD is present in the active form of FOX but that its autocatalytic formation is crucial for activity. As a result, formate oxidase serves as the first enzyme reported to have an active 8-formyl FAD as a cofactor. The FOX bound 8-formyl FAD was also shown to form a highly stable anionic semiquinone when exposed to light.

Formate oxidases have been identified in several organisms including *Aspergillus nomius* IRI013, *Debaryomyces vanrijiae* MH201, and *Aspergillus oryzae* RIB40.

In an aspect, the formate oxidase is FOX from *A. oryzae* RIB40 having SEQ ID NO: 2.

```
                                             (SEQ ID NO: 2)
MATDGSHFDFVIVGGGTAGNTVAGRLAENPNVTVLIVEAGIGNPEDIPEI

TTPSSAMDLRNSKYDWAYKTTMVRRDDYERIEKPNTRGKTLGGSSSLNYF

TWVPGHKATFDQWEEFGGKEWTWDPLVPYLRKSATYHDDPRLYSPELEKI

GGGGPIPISHAELIDEMAPFRENLTKAWKSMGQPLIENIYDGEMDGLTHC

CDTIYRGQRSGSFLFVKNKPNITIVPEVHSKRLIINEADRTCKGVTVVTA

AGNELNFFADREVILSQGVFETPKLLMLSGIGPTRELSRHGINTIVDSRH
```

-continued

```
VGQNLMDHPGVPFVLRVKDGFGMDDVLLRHGPKRDAVVSAYNKNRSGPVG

SGLLELVGFPRIDKYLEKDAEYRKAKAANGGKDPFSPLGQPHFELDFVCN

IFGTAFQWHFPTPKTGDHLTVVVDLVRPISDPGEVTLNSADPFQQPNINL

NFFANDLDIIAMREGIRFSYDLLFKGEGFKDLVESEYPWEMPLDSDKEMH

RAVLDRCQTAFHPTGTARLSKNIDQGVVDPKLKVHGIKKLRVADASVIPI

IPDCRIQNSVYAVGEKCADMIKAEHKDLY
```

The alcohol/aldehyde oxidase and the formate oxidase are typically present in the coating in an activity ratio range of 1:1 to 1:5 FOX activity to AOX activity.

The alcohol/aldehyde oxidase and the formate oxidase are immobilized on a solid particulate support. Exemplary solid particulate supports include a carbohydrate, an inorganic material, an organic material, a synthetic organic material, or combinations of the above materials to which an enzyme is capable of being immobilized. Organic materials include, but are not limited to agarose; agarose derivatives containing amino, carboxyl, epoxy or hydrazide functional groups; polyacrylamide; polyacrylamide derivatives containing amino, carboxyl, epoxy or hydrazide functional groups; and the like. Inorganic solid particulate supports include silicas; aluminosilicates (e.g., zeolites); aluminum oxides; carbon or graphite particles; carbon or graphite particles to which are adsorbed platinum group metals such as platinum, palladium or rhodium; carbon or graphite particles to which are adsorbed platinum group metal oxides; inorganic materials to which primary, secondary, or tertiary amine functional polymers have been adsorbed; inorganic materials to which quaternary ammonium polymers such as Merquat® (Quaternium-40) have been adsorbed; and the like. Moreover, combinations of inorganic and organic materials from which the solid particulate support can be selected include, but are not intended to be limited to carbon or graphite particles to which are adsorbed metalloporphyrins such as, for example, cobalt protoporphyrin.

In an aspect, the solid particulate support comprises silica particles, such as mesocellular silica foams, porous silica microspheres, porous core-shell particles, porous silica nanoparticles, particles with a porous silica layer, or a combination comprising at least one of the foregoing.

In an aspect, the solid particulate support, e.g., an inorganic particulate support, has a particle diameter of 0.1 to 800 micrometers, preferably 0.5 to 100 micrometers, and a pore diameter of 50 Angstroms to 200 nanometers, preferably 100 Angstroms to 50 nanometers.

The enzymes can be attached to the solid particulate support according to methods well known in the art. Such methods include, but are not limited to, adsorption, ionic binding, covalent binding, and the like.

An enzyme can be immobilized to a solid particulate support by adsorption of the enzyme to the solid particulate support to form a solid particulate support/enzyme complex. Generally, adsorbing an enzyme to the solid particulate support is accomplished according to methods well known in the art. It will be understood, of course, that the adsorptive properties displayed by enzymes toward solid particulate supports are a function of the pH and ionic strength of the buffer containing the two entities. In order to achieve proper adsorption, the pH and ionic strength of a buffer containing an enzyme and a solid particulate support can vary according to the specific enzyme or specific solid particulate supports being used. In an aspect, the enzyme is dissolved in a solid particulate support mixture such that its concentration in the solution will saturate the non-specific binding sites on the surface of the particular solid particulate support. Thus, the pH and ionic strength of the buffer is preferably that which will provide maximal adsorption of the enzyme to the solid particulate support.

Immobilization of an enzyme to a solid particulate support can generally be accomplished by exploiting the attractive forces associated with a charged enzyme and an oppositely charged solid particulate support, to thereby form a solid particulate support/enzyme complex. For example, a cationic solid particulate support, wherein a positively charged compound is adsorbed or covalently bound to the solid particulate support, is reacted with an anionic enzyme to obtain an enzyme/solid support complex. Compounds which are suitable for conferring a positive charge upon a solid particulate support include, but are not intended to be limited to, quaternary ammonium polymers such as Merquat® (Quaternium-40); amine functional polymers such as polyethylene-imine; and the like. Adsorption of these compounds to the solid particulate support readily occurs by adding an excess of the compound, dissolved in a suitable solvent, to the solid particulate support. After a sufficient time has elapsed, the solid particulate support can be collected, for example, by filtration or centrifugation. Any residual compound can be separated from the solid particulate support by rinsing the solid particulate support with a suitable solvent, then re-collecting the solid phase. The rinsed solid particulate support can then be used wet or can be dried before an enzyme is ionically bound to it.

Although there are anionic enzymes and proteins that will inherently ionically bind a cationic solid particulate support, it is possible to anionically modify an enzyme so that more ionic bonds can be formed between the enzyme and the solid particulate support.

One method for providing a negative charge to, for example, an enzyme is by reacting it with, for example, an aliphatic or aromatic carboxylic acid anhydride. Such carboxylic acid anhydrides include, but are not intended to be limited to pyromellitic dianhydride, succinic anhydride, maleic anhydride, and the like.

A negative charge can be provided to an enzyme by reacting pyromellitic dianhydride with positively charged amino groups, wherein the amino groups present on the enzyme can be converted to aromatic tricarboxylates which have three negative charges. This conversion can be carried out by adding an aqueous suspension of pyromellitic dianhydride to a solution of enzyme. The enzyme or protein can be dissolved in an appropriate buffer having a pH of about 6.5 to about 8.0, such as about 7.0 to about 7.5. The quantity of pyromellitic dianhydride can be about 0.05 to about 0.5 times more than the quantity of the enzyme, such as about 0.05 to about 0.15 times more than the quantity of the enzyme. Although the conversion of the amino group to the aromatic tricarboxylate is typically complete within about 5 minutes, the reaction can be allowed to incubate at an ambient temperature for about 10 minutes to about 20 minutes. The reaction mixture can then be added directly to a cationic solid support or purified before being reacted with a cationic solid particulate support.

Since the enzyme and the solid particulate support carry opposite charges, an ionic bond between the two entities will readily form. Typically, the charged solid particulate support will have high capacity for binding an anionically charged enzyme. The enzyme can be at a concentration that will saturate the cationic binding sites on the solid particulate support. When a suspension of cationically charged solid particulate support is added to a solution of anionically charged enzyme to form a reaction mixture, it is preferred that the ratio of enzyme to solid particulate support is about 1:1.5 to about 1:5. The reaction can be carried out in a low ionic strength buffer which has a pH of about 6.5 to about 7.5, for about 1 minute to about 30 minutes, and at a temperature of about 2° C. to about 25° C. The enzyme/solid particulate support complex thus formed can be separated from the unbound enzyme by methods well known to those skilled in the art, and either added to the binding reagent or left in the reaction mixture, and then added directly to the latex binder. In cases where the complexes are separated from the reaction mixture, the reaction mixture can be filtered using a filter having a pore size small enough to trap the enzyme/solid particulate support complexes, yet large enough to allow unbound enzyme to flow through the filter. Alternatively, the complexes can be centrifuged to form a wet pellet. To ensure that all of the unbound enzyme is removed from the complexes, the captured complexes can be washed with low ionic strength buffer having a pH from between about 6.0 and about 7.5.

Alternatively, an enzyme and solid particulate support can be ionically bound and co-precipitated from a solution in a single step. Generally, this precipitation is accomplished by first making a single solution of enzyme and solid particulate support, treating the solution with pyromellitic dianhydride, and then treating the solution with one of the positively charged polymers described above. The ratio of enzyme to solid particulate support can be about 1:1 to about 1:5 and the quantity of pyromellitic dianhydride in the solution can be about 0.05 to 0.15 times the quantity of the enzyme in the solution.

The manner by which an enzyme can be ionically bound to a solid particulate support is not intended to be limited to the methods described herein, and that other methods known in the art can be employed as well.

In another aspect, an enzyme can be immobilized to a solid particulate support by a covalent bond which is formed between enzyme and the solid particulate support to form an enzyme/solid particulate support complex. In order to form such a covalent bond, the solid particulate support can be modified to enable it to form a covalent bond with an enzyme. Such modifications to the solid particulate support include, but are not limited to, adding functionalities such as amine groups, carboxylate groups, epoxide groups, and the like, to the solid particulate support. For example, silica can be derivatized with aminopropyl triethoxy silane or polyethylene-imine, using methodologies well known to those skilled in the art. After such modification has been completed, the aminated solid particulate support can be further derivatized to introduce other functional groups by methods well known in the art. Enzymes can then be covalently bound to a derivatized solid particulate support using methods well known in the art. For example, use of a water soluble carbodiimide such as 3 ethyl 1-(3-dimethylaminopropyl) carbodiimide, or a similar carboxylate activating agent, can be added to an appropriate buffer containing a modified solid particulate support and an enzyme to yield a covalently bound enzyme/solid particulate support complex which is formed via an amide bond between the carboxylate and amino groups.

Alternatively, a modified solid particulate support can be reacted, as above, with a modified enzyme. Such modified enzymes include, but are not intended to be limited to, those modified with pyromellitic dianhydride as described previously, or other mono- or polyanhydrides, such as N-carboxy-alpha-amino acid anhydrides, and the like using methods well known in the art.

In another method of covalently binding the enzyme to the solid particulate support, heterobifunctional coupling compounds, which are well known in the art, can be used. Such compounds include, but are not intended to be limited to, m-maleimidobenzoyl-N-hydroxysuccinimide ester (MBS), sulfosuccinimidyl 4-(p-maleimidophenyl) butyrate (S-SMPB), m-maleimidobenzoylsulfosuccinimide ester (S-MB S), N-γ-maleimidobutyryloxysuccinimide ester (GMBS), succinimidyl 4-(N-maleimidomethyl) cyclohexane 1-carboxylate (SMCC), those found in U.S. Pat. No. 4,994,385, and the like. Methods of using such compounds to covalently couple two compounds are well known in the art.

Formate oxidase can be present in the coating in a dry weight amount from about 0.08 to about 8 wt. %, and more specifically about 0.2 to about 5 wt. % of the coating, based on the total weight of the coating. Alcohol/aldehyde oxidase can be present in the coating composition in a dry weight amount from about 0.1 to about 10 wt. %, and more specifically about 0.5 to about 8 wt. % of the coating, based on the total weight of the coating. The solid particulate support can be present in the coating in a dry weight amount from about 2 to about 45 wt. %, and more specifically about 10 to about 40 wt. % of the coating, based on the total weight of the coating.

Formate oxidase can be present in the liquid coating composition in a dry weight amount from about 0.01 to about 5 wt. %, and more specifically about 0.1 to about 3 wt. % of the liquid coating composition, based on the total weight of the liquid coating composition. Alcohol/aldehyde oxidase can be present in the liquid coating composition in a dry weight amount from about 0.05 to about 5 wt. %, and more specifically about 0.2 to about 4 wt. % of the liquid coating composition, based on the total weight of the liquid coating composition. The solid particulate support can be present in the liquid coating composition in a dry weight amount from about 1 to about 25 wt. %, and more specifically about 5 to about 20 wt. % of the liquid coating composition, based on the total weight of the liquid coating composition.

After the enzymes have been immobilized to a solid particulate support to form enzyme/solid particulate support complexes, the complexes are combined with a liquid latex binder to form a liquid coating composition for forming a coating. One or more different species of enzyme/solid particulate support complexes can be dispersed throughout the latex binder when forming the coating. For example, one type of enzyme immobilized to a solid particulate support can be added to an immobilization medium containing a second type of enzyme immobilized to a solid particulate support.

A suspension of the enzyme/solid particulate support complex can be added directly to the latex binder or collected and washed before adding to the latex binder. The method of physical dispersion of the enzyme/solid particulate support material in the latex binder can affect the properties of the coatings. It is therefore preferred that the enzyme/solid particulate support complexes are well dispersed in the latex binder in order to form a homogeneous mixture. Methods for dispersing the complexes include, but are not intended to be limited to high shear homogenization, ball milling and the like.

Preferably the liquid latex binder is aqueous, and in a liquid or fluid form, wherein the enzyme/solid particulate support complex is evenly dispersed or dispersable therein. The latex binder is selected to enable the enzyme/solid particulate support complexes to adhere to a surface when dried thereon. In an embodiment, the latex binder is selected to irreversibly adhere to the surface when dried thereon. The latex binder is further selected to dry to a physically durable coating, preferably a water resistant coating, which retains the biological activity of the enzymes. In a preferred embodiment, the latex binder is selected to adhere to a variety of surfaces, including, but not intended to be limited to smooth or non-porous, as well as porous surfaces.

The latex binder can be derived from monomers comprising vinyl acetate or at least one acrylic monomer such as acrylic acid, acrylic acid $C_{1-10}$ alkyl esters, methacrylic acid, or methacrylic acid $C_{1-10}$ alkyl esters, optionally copolymerized with one or more of styrene, hydroxyethyl acrylate, hydroxypropyl acrylate, α-methyl styrene, vinyl chloride, acrylonitrile, methacrylonitrile, ureido methacrylate, vinyl acetate, vinyl esters of branched tertiary monocarboxylic acids (e.g., vinyl esters of versatic acid (referred to as vinyl versatates) commercially available under the trademark VeoVa® from Shell Chemical Company or sold as Exxar® Neo Vinyl Esters by ExxonMobil Chemical Company), itaconic acid, crotonic acid, maleic acid, fumaric acid, and ethylene. It is also possible to include $C_{4-8}$ conjugated dienes such as 1,3-butadiene, isoprene, and chloroprene. In an embodiment, the monomers include one or more of n-butyl acrylate, methyl methacrylate, styrene, and 2-ethylhexyl acrylate.

Pure acrylics can be used (comprising acrylic acid, methacrylic acid, an acrylate ester, and/or a methacrylate ester as the main monomers); styrene-acrylics (comprising styrene and acrylic acid, methacrylic acid, an acrylate ester, and/or a methacrylate ester as the main monomers); vinyl-acryls (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, optionally with one or more monomers such as itaconic acid and ureido methacrylate.

Specific examples of latex binders that can be used in the liquid coating compositions (and thus the coatings) include, but are not limited to, an acrylic latex (including carboxylate acrylic latexes), acrylonitrile-butadiene latex, alkyd latex, ethylene-vinyl acetate latex, neoprene latex, polyamide latex, polybutadiene latex, polybutylene latex, polychloroprene latex, polyester latex, polyisoprene latex, polypropylene latex, polyurethane latex, polyvinyl acetate latex, polyvinyl alcohol latex, polyvinyl butyral latex, polyvinyl chloride latex, polyvinylidene chloride latex, silicone emulsion latex, styrene-acrylic latex, styrene-acrylonitrile latex, styrene-butadiene rubber latex, styrene-isoprene latex, and the like, or a combination comprising at least one of the foregoing. Preferably, the latex binder comprises an acrylic latex, a styrene-acrylic latex, vinyl-acryl latex, vinyl acetate latex, or a combination comprising at least one of the foregoing.

The latex binder can be present in the liquid coating composition in a dry weight amount from about 5 to about 80 wt. %, and more specifically about 8 to about 60 wt. % of the liquid coating composition, based on the total weight of the liquid coating composition.

In an advantageous feature, it has been found that use of a particular class of polyhydroxy compounds, in particular certain carbohydrates, can significantly increase the stability of the immobilized enzyme complex. Optionally, one or more of the enzymes is freeze-dried in the presence of the stabilizer, although freeze-drying is not required. The carbohydrate can be a monosaccharide, disaccharide, or oligosaccharide containing 3 to 10 monosaccharide units. Exemplary enzyme stabilizers include sucrose, trehalose, mannitol, sorbitol, xylose, xylitol, mannose, raffinose, lactose, maltose, galactose, or a combination comprising at least one of the foregoing. In a preferred embodiment, the stabilizer is sucrose, trehalose, mannitol, sorbitol, or a combination comprising at least one of the foregoing The amount of the carbohydrate stabilizer is selected to improve the stability of the enzymes in the liquid coating composition, and optionally in the coating, while not significantly adversely affecting the desired properties of the liquid coating composition and the coating. In an aspect, the enzyme stabilizer can be used in the liquid coating composition in an amount from about 1 to about 15 wt. %, specifically about 1 to about 5 wt. % of the silica support in the liquid coating composition.

The liquid coating composition can also contain supplemental components that can provide the coating with desired properties, enhance the stability of the immobilized enzyme or improve the capability of the coating to dry to a substantially water resistant or insoluble layer. The supplemental components are selected so as to not significantly adversely affect the desired properties of the liquid coating compositions and the coatings, in particular stability of the enzymes. Such supplemental components include, but are not limited to, latex formulation stabilizers, coalescing solvents, plasticizers, rheology modifiers, thickeners, film forming agents, surfactants, preservatives, biocides, mildewcides, dispersing agents, defoaming agents, drying retarder, colorants, extending agents, pH adjusters waxes, or a combination comprising at least one of the foregoing. The supplemental components are present in the amount ordinarily used in liquid latex coating compositions, and particularly in latex paint compositions.

In preferred embodiments, the coatings include a colorant, which as used herein includes dyes and pigments. The term "pigment" as used herein includes non-film-forming solids such as extenders and fillers, for example an inorganic pigment $TiO_2$ (in either anatase and rutile forms), clay (aluminum silicate), $CaCO_3$ (in both ground and precipitated forms), aluminum oxide, silicon dioxide, magnesium oxide, talc (magnesium silicate), barites (barium sulfate), zinc oxide, zinc sulfite, sodium oxide, potassium oxide, solid (high Tg) organic latex particles added to modify hardness or surface roughness or (as in the case of hollow latex particles) to replace $TiO_2$, or a combination comprising at least one of the foregoing. Representative combinations include blends of metal oxides such as those sold under the marks MINEX® (oxides of silicon, aluminum, sodium and potassium commercially available from Unimin Specialty Minerals), CELITES® (aluminum oxide and silicon dioxide commercially available from Celite Company), ATOMITES® (commercially available from Imerys), and ATTAGELS® (commercially available from BASF). Specifically, the pigment includes $TiO_2$, $CaCO_3$, or clay. Generally, the mean particle sizes of the pigments can be about 0.01 to about 50 micrometers. For example, the $TiO_2$ particles used in the aqueous coating composition typically have a mean particle size from about 0.15 to about 0.40 micrometers. The pigment can be added to the liquid coating composition as a powder or in slurry form. The pigment can be used in the liquid coating composition in an amount from about 5 to about 75 wt. %, specifically about 10 to about 55 wt. % of the total solids in the liquid coating composition.

Although much of the water is present in the latex binder and in other components of the liquid coating composition, water can be added separately to the liquid coating composition. Typically, the liquid coating composition includes about 10 to about 85 wt. % and more specifically about 20 to about 80 wt. % water, i.e., the total solids content of the liquid coating composition is about 15 to about 90 wt. %, more specifically about 20 to about 80 wt. % of the total composition. The liquid coating compositions are typically formulated such that the hardened (dried) coatings comprise at least about 5 volume % (vol. %) dry polymer solids, and, when present, about 5 to about 90 vol. % of non-polymeric solids in the form of pigments.

Plasticizers can be used to improve film formation or to prevent cracking of the coating. Exemplary plasticizers include those such as dibutyl phthalate and dioctyl sebacate. Thickeners can be used to prevent settling of the suspended solids, and can be thickeners such as hydroxyethylcellulose, silica and ACRYSOL™ SCT 200. Film forming agents, typically organic solvents that are also known as coalescing solvents, can solubilize plasticizers and control the rate of drying so that smooth coatings result. Film forming agents such as 2-ethoxyethanol, ethyleneglycol monopropyl ether, and 2-(2-butoxyethoxy) ethanol can be used. Dispersing agents can prevent polymer aggregation, and include, for example TRITON™ X-100 detergent. Defoaming agents can reduce foaming during mixing, and include, for example, defoaming agents such as 2-octanol.

In another aspect, a method for forming a coating comprises applying a liquid coating composition that comprises an aldehyde oxidase and a formate oxidase immobilized on a solid particulate support, and a liquid latex binder onto a substrate; and drying the liquid composition to form the coating.

The liquid coating composition can be readily dispensed or applied to a surface by various methods. Thus, for example, the liquid coating composition can be dispensed or applied to a surface by brushing, pumping, liquid metering, screen printing, spraying, jetting, or dipping the surface into the liquid coating composition.

Drying can be by exposure to ambient conditions after coating. Other techniques, such a flow of forced air or heat can be used, although the amount of heat should be controlled to not significantly adversely affect enzyme activity. Furthermore, since the latex binder can be dried at ambient temperatures, the enzyme/solid phase complexes are not exposed to harsh temperatures that can denature the enzyme component. Still further, a surface to which the latex binder has been applied and dried is reusable because the latex binder dries to a water resistant adherent layer. Moreover, the latex binder is not limited by the types of surfaces to which it is applied.

In an aspect, the coating is a paint for a building interior.

In an aspect, the coating exhibits color stability. For example, in an embodiment there is a color difference quantified by CIELAB metric DE of less than 5, preferably less than 2 as measured by ASTM D2244 compared to a non-enzyme containing control.

In another aspect, the coating abates formaldehyde in the air with an abatement efficiency as defined by at least 75% removal of starting levels of formaldehyde in the air as determined spectrophotometrically by Test method JC/T 1074-2008.

In an aspect, the coating is effective to convert formaldehyde to carbon dioxide for at least 26 weeks, 104 weeks, or 60 months when maintained in a temperature range of about 40-80° F.

A method for converting atmospheric formaldehyde to carbon dioxide comprises contacting a coating as described herein with an atmosphere comprising formaldehyde and converting at least a portion of the formaldehyde to carbon dioxide.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Nucleic acid sequences and polypeptide sequences can have substantial homology to the specific nucleic acid sequences and amino acid sequences recited herein.

The enzymes described herein include enzymes having "conservative sequence modifications," amino acid sequence modifications which do not affect or alter the above-mentioned characteristics of the enzymes.

This disclosure is further illustrated by the following examples, which are non-limiting.

EXAMPLES

Example 1

Preparation of Formate Oxidase (FOX)

Cloning, expression, and purification of his-tagged FOX. The following synthesized cDNA sequence for FOX from *A. oryzae* RIB40 was purchased from GeneArt® (Life Technologies, Grand Island, N.Y.).

```
                                        (SEQ ID NO: 3)
ATGGCAACCGATGGTAGCCATTTTGATTTTGTTATTGTTGGTGGTGGCAC

CGCAGGTAATACCGTTGCAGGTCGTCTGGCAGAAAATCCGAATGTTACCG

TTCTGATTGTTGAAGCCGGTATTGGTAATCCGGAAGATATCCCGGAAATT

ACCACCCCGAGCAGCGCAATGGATCTGCGTAATAGCAAATATGATTGGGC

CTATAAAACCACCATGGTTCGTCGTGATGATTATGAACGTATTGAAAAAC

CGAATACCCGTGGTAAAACCCTGGGTGGTAGCAGCAGCCTGAACTATTTT

ACCTGGGTTCCGGGTCATAAAGCAACCTTTGATCAGTGGGAAGAATTTGG

TGGTAAAGAATGGACCTGGGATCCGCTGGTTCCGTATCTGCGCAAAAGCG

CAACCTATCATGATGATCCGCGTCTGTATAGTCCGGAACTGGAAAAAATT

GGTGGCGGTGGTCCGATTCCGATTAGCCATGCAGAACTGATTGATGAAAT

GGCACCGTTTCGTGAAAATCTGACCAAAGCATGGAAAAGCATGGGTCAGC

CGCTGATTGAAAACATTTATGATGGTGAAATGGATGGCCTGACCCATTGT

TGTGATACCATTTATCGTGGTCAGCGTAGCGGTAGCTTTCTGTTTGTTAA

AAACAAACCGAACATTACCATTGTGCCGGAAGTTCATAGCAAACGCCTGA

TTATTAACGAAGCAGATCGTACCTGTAAAGGTGTTACCGTGGTTACCGCA

GCAGGTAATGAACTGAACTTTTTTGCAGATCGTGAAGTGATTCTGAGCCA
```

-continued
```
GGGTGTTTTGAAACCCCGAAACTGCTGATGCTGAGTGGTATTGGTCCGA

CCCGTGAACTGAGCCGTCATGGCATTAATACCATTGTTGATAGTCGTCAT

GTTGGCCAGAATCTGATGGATCATCCGGGTGTTCCGTTTGTTCTGCGTGT

TAAAGATGGTTTTGGTATGGATGATGTTCTGCTGCGTCATGGTCCGAAAC

GTGATGCAGTTGTTAGCGCATATAACAAAAATCGTAGCGGTCCGGTTGGT

AGCGGTCTGCTGGAACTGGTTGGTTTTCCGCGTATTGATAAATACCTGGA

AAAAGATGCCGAATATCGTAAAGCAAAAGCAGCAAATGGTGGCAAAGATC

CGTTTAGTCCGCTGGGCCAGCCGCATTTTGAACTGGATTTTGTTTGTATG

TTTGGCACCGCCTTTCAGTGGCATTTTCCGACCCCGAAAACCGGTGATCA

TCTGACCGTTGTTGTTGATCTGGTTCGTCCGATTAGTGATCGGGTGAAG

TTACCCTGAATAGTGCCGATCCGTTTCAGCAGCCGAATATTAACCTGAAT

TTTTTCGCCAACGATCTGGACATTATTGCAATGCGTGAAGGTATTCGCTT

TAGCTATGATCTGCTGTTTAAAGGCGAAGGCTTTAAAGATCTGGTTGAAA

GTGAATATCCGTGGGAAATGCCGCTGGATAGCGATAAAGAAATGCATCGT

GCAGTTCTGGATCGTTGTCAGACCGCATTTCATCCGACCGGCACCGCACG

TCTGAGCAAAAACATTGATCAGGGTGTTGTGGATCCGAAACTGAAAGTTC

ATGGTATCAAAAAACTGCGTGTTGCAGATGCAAGCGTTATTCCGATCATT

CCGGATTGTCGTATTCAGAATAGCGTTTATGCAGTGGGTGAAAAATGTGC

CGATATGATTAAAGCCGAACACAAAGACCTGTAT.
```

The synthesized gene, which included optimized codon usage for expression in *Escherichia coli*, was inserted into the NdeI-NotI restriction sites of the pET21c(+) expression vector (EMD Bioscience, Darmstadt, Germany) and transformed into *E. coli* Novablue™ cells (EMD Bioscience). After isolating the plasmid DNA from the *E. coli* Novablue™ and sequencing to verify the presence of the recombinant FOX$_{AO}$ gene, the resulting pET21-FOX$_{AO}$ was transformed into *E. coli* BL21 (DE3) expression host strain (EMD Bioscience). Expression and purification of his-tagged FOX$_{AO}$ was then performed as previously described with the following modifications: harvested cells were suspended in 25 mM potassium phosphate buffer, pH 7.5, supplemented with 20 mM imidazole, 100 mM NaCl, and 10% glycerol prior to sonication. This supernatant was then applied unto a column of HisPur™ Ni-NTA resin equilibrated with the aforementioned suspension buffer before being washed, eluted, dialyzed, and stored as previously described but modified so that all steps were performed in the absence of light.

Construction expression, and purification of FOX without His-Tag. A recombinant pET21C(+) plasmid containing the FOX gene sequence was used to construct a FOX enzyme without a His-tag using site-directed mutagenesis. Primers for non His-tagged FOX were designed as 33 base oligonucleotides with the following sequences CACAAAGACCTGTATTAAGCCGCACTGGAGCAC (SEQ ID NO: 4) and GTGCTCGAGTGCGGCTTAATACAGGTCTTTGTG (SEQ ID NO: 5). Using these primers for site-directed mutagenesis, the GCG codon immediately following the C-terminal amino acid of the FOX gene sequence contained in the pET21C(+) plasmid was replaced with a TAA stop codon, thus eliminating inclusion of the C-terminal His-tag amino acid sequence in the expressed protein. The sequence of the non His-tagged FOX gene was confirmed by DNA sequencing analysis at Eurofins MWG Operon LLC (Huntsville, Ala.). Plasmids with confirmed sequence were transformed into *E. coli* BL21(DE3) competent cells for protein expression and stored at −80° C. *E. coli* BL21(DE3) cells from frozen stocks containing the appropriate over-expression plasmid were isolated on LB-agar plates containing 100 μg/mL ampicillin (LB-Amp). A single colony of *E. coli* BL21(DE3) containing the appropriate expression plasmid was used to inoculate 5 mL LB-Amp media which were incubated overnight at 37° C. A 1% inoculum of the 5 mL culture was used to inoculate 100 mL LB-Amp media which was incubated 8 hrs at 37° C. and used to inoculate four 2.8 L Erlenmeyer flasks containing 1000 ml of LB-Amp media. Cultures were incubated at 30° C. and 130 rpm until they reached an OD600 between 0.6-0.8, at which point they were induced by the addition of isopropyl-b-D-1-thiogalactopyranoside to a final concentration of 25 μM and incubated for a further 12 h at 30° C. with constant shaking (130 rpm). Cells were collected by centrifugation for 15 min at 5000 g and 4° C., and stored at −80° C. as frozen pellets for 1 hr. About 8 g of wet cells were collected from each 1000 ml culture.

For the purification of non his-tagged FOX, cells from the 4 L growths were resuspended in 100 mL of 25 mM potassium phosphate buffer, pH 7.5, supplemented with 100 mM NaCl, 10% glycerol, and 4 μg/mL lysozyme. Cell lysis was performed by sonication, followed by the addition of 1.5% streptomycin sulfate to precipitate nucleic acids. Ammonium sulfate precipitation was from 50% to 70%. The pelleted protein from the 70% ammonium sulfate precipitation was resuspended in 10 mL of 25 mM potassium phosphate buffer, pH 7.5, supplemented with 100 mM NaCl and dialyzed twice against 10 mM sodium acetate buffer, pH 4.0, supplemented with 100 mM NaCl. Following dialysis, the sample was centrifuged at 10,000 g to remove debris, and stored at 4° C. until needed.

Determination of FOX concentrations. The total protein concentration of the purified FOX enzyme stock was determined by Bradford assay using Coomassie protein assay reagent with bovine serum albumin as the standard. The molar ratio of 8-fFAD to FOX was determined by extracting 8-fFAD from FOX through heat denaturation at 100° C. for 10 min, centrifuging the precipitate, and estimating the total 8-fFAD concentration of the lysate using the molar extinction coefficient of 9000 $M^{-1}$ $cm^{-1}$ at 450 nm as described in the art. From these measurements, the molar extinction coefficient of active, flavin bound FOX was determined to be 10,200 $M^{-1}$ $cm^{-1}$ at 472 nm.

FOX activity assays. FOX activity assays were conducted using a Hansatech Oxygraph equipped with the DW1 electrode chamber and S1 electrode to determine the initial rate of $O_2$ consumption in solutions employing 0.2 μM flavin-bound FOX, dissolved oxygen (0.22 mM) and sodium formate (100 mM) in 50 mM acetate (pH 4.0). All assays were performed at 25° C. and in triplicate.

An example of purified FOX used in technology: Four (4) liters of BL21(DE3) culture containing the recombinant his-tagged WT FOX$_{AO}$ gene was grown, and his-tagged WT FOX was expressed and purified as described above. The purification resulted in 3 mL of bright yellow solution containing 14 mg/mL FOX enzyme solution. This stock enzyme solution was used for silica loading as described below.

Example 2

Preparation of Alcohol/Aldehyde Oxidase (AOX)

Growing wildtype GS113 Pichia strain under induction of methanol leads to overproduction of AOX in peroxisomes.

AOX containing cell mass was harvested and stored at −80° C. Cells were disrupted to release AOX using a bead beater and glass beads and the soluble AOX was purified using fractionated ammonium sulfate precipitation with subsequent rebuffering and PEG 4000 precipitation to concentrate AOX. AOX can be resolubilized after PEG 4000 treatment, other proteins cannot. To further enhance AOX capabilities, AOX can be stabilized using either 45% sucrose or 45% trehalose as an excipient. Different formulations have shown to enhance stability of AOX. The enzyme can be used in its liquid form or freeze-dried and then either resolubilized or applied in its dried form. Any of these preparations can then be used for alcohol or aldehyde abatement, specifically formaldehyde abatement, using the assay described herein.

Example 3

Fermentation, Purification and Cloning of New Variants of AOX from *Pichia pastoris* (*Komagataella pastoris*)

*Pichia pastoris* strain GS113 was used for 6 L fermentation using a classic Pichia protocol as previously described. A semi-defined media was used to ferment the strain and produce AOX. The media consisted of basal salts medium supplemented with glycerol, phosphoric acid and trace salts, see Table 1. Fermentation was inoculated with a 200 ml overnight culture and after 48 h, a glycerol feed at 18 ml/hr/L of a 50% glycerol stock was applied for 8 h until *Pichia pastoris* reached mid to end log phase and stopped consuming oxygen at a high rate. The pH value was adjusted to 4.5 throughout the fermentation using a concentrated ammonia feed (28% NH3). The feed was regulated via the $pO_2$ rate, induction of AOX was initiated by methanol feed in an increasing controlled manner (increasing feed between 1 ml/h/L up to 3 ml/h/L) and continued for an additional 48 h. The cells were then harvested and stored at −80° C.

TABLE 1

Fermentation basal salts medium, pH adjusted to 4.5 with 28% ammonia solution

| Component | g/L (for 1 L fermentation medium) |
|---|---|
| Phosphoric acid 85% | 26.7 |
| Calcium sulfate | 0.93 |
| Potassium sulfate | 18.2 |
| Magnesium sulfate × 7 $H_2O$ | 14.9 |
| Potassium hydroxide | 4.13 |
| Glycerol | 40 |
| Tap water, not distilled | To 1 liter |

*Pichia pastoris* cells were broken up using a bead beater (Hamilton Beach) and glass beads Zirkon 0.5 mm (Biospec) in the presence of 50 mM HEPES pH 6.5+10 mM KCl+5 mM $MgCl_2$+50 mM NaCl+5% glycerol in a 50/50 mixture of beads and cell suspension at 4° C. The resulting crude extract was separated from debris using centrifugation and then a series of ammonium sulfate precipitations was applied, first up to 35%, then 45% and lastly, 60%. AOX precipitated mostly at 45%, and some of it at 60% together with catalase.

The salted out protein was buffered against 10 mM $Na_2HPO_4$/citric acid pH 8.0 and 10% PEG 4000 was added, which precipitated all proteins out. AOX was recovered after centrifugation by dissolving in 10 mM $Na_2HPO_4$/citric acid pH 8.0 followed by centrifugation of the undissolved, precipitated contaminants. This preparation was sufficiently pure for further experiments.

Figure 3:
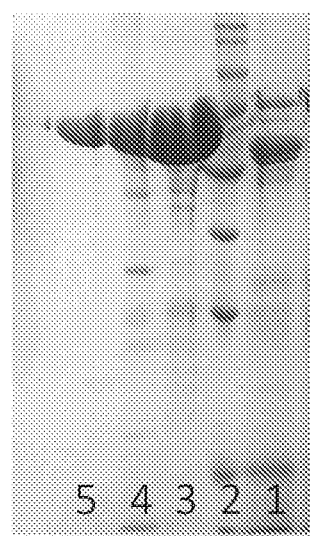
FIG. 3 shows the increase in purity of AOX during the purification procedure.

To obtain even purer AOX, this preparation was used for column chromatography involving a phenylsepharose column with 1.5 M $(NH_4)_2SO_4$ in 50 mM TEA pH 8.0 and a decreasing salt gradient. AOX eluted at 0.6 M $(NH_4)_2SO_4$. The different steps are highlighted in FIG. 1. FIG. 3 shows from right to left the increase in purity of AOX (prominent band at 80 kD) from crude preparation (lane 1) to phenylsepharose chromatography (lane 5). Complete purity was achieved after the final step. Lane 1: crude extract, lane 2: protein marker (Novagen), lane 3: 45% $(NH_4)_2SO_4$ precipitation, lane 4: 60% $(NH_4)_2SO_4$ precipitation, lane 5: phenylsepharose.

AOX protein concentration was determined using the Bradford method with Coomassie G250 and bovine serum albumin as a standard. AOX activity was measured by determination of hydrogen peroxide formation, which is stoichiometrically formed during alcohol/aldehyde oxidation. 10 mM formaldehyde was added to a substrate solution of 0.6 mM 4-aminoantipyrine and 7 mM phenol in 0.2 M $Na_2HPO_4$/citric acid pH 8.0 and 0.14 mg horseradish peroxidase (24 U/mg). 10 μl of AOX was added to start the reaction, quinoneimine dye formation was spectrophotometrically observed at 500 nm as described in the art.

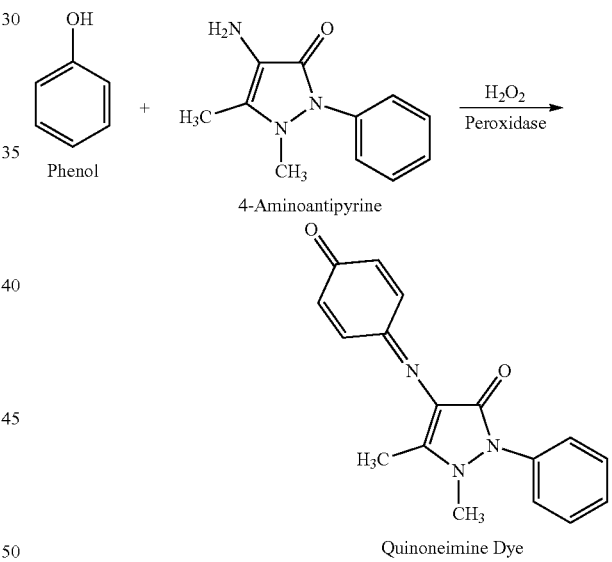

Scheme 1: Assay for Activity of AOX, Based on the Formation of Quinoneimine Dye

Cloning of AOX variants: New variants of AOX, specifically variants to improve thermostability, such as R241K within the sequence of AOX, can be generated to improve formaldehyde abatement. Variants were generated using standard site-directed mutagenesis protocols combined with overlap PCR and then cloned and screened in *E.coli*. Positive mutants that have incorporated the mutation were then selected to be transformed into AOX-deficient *Pichia pastoris* strains such as KM71H and then tested for activity. For each possible mutation 3 different clones from the *Pichia pastoris* transformation were expressed and activities compared. The one with the highest activity was selected and tested for thermostability.

The AOx1 gene was isolated from *Pichia pastoris* using an RNA preparation and cDNA conversion protocol. Briefly, RNA was isolated from an overnight culture of *Pichia pastoris*, induced with 0.5% methanol. The RNA was isolated using the RNeasy® purification kit (Qiagen). The RNA was immediately used in a reverse transcription reaction using MMLV transcriptase and the Advantage™ RT for PCR kit (Clontech). The resulting cDNA was used in a regular PCR with AOX-specific primers to obtain the AOX gene out of the cDNA pool. The gene was then cloned into the Electra™ vector p902 using the Electra™ cloning kit (DNA2.0) and resulting positive clones were transformed into competent *Pichia* pastoris KM71H cells (AOX1-deficient). Clones were then tested for AOX activity. Variants of AOX were generated using gene specific mutation primers and the overlap PCR protocol. The resulting mutated AOX gene was again cloned into p902 and then after positive clone selection in *E.coli*, the resulting variant AOX plasmid was transformed into competent *Pichia pastoris*.

Example 4

Thermal Stability of R241K AOX

The inventors identified R241K AOX as a thermostable AOX variant. While both WT and R241K variant AOX have activity after lyophilization and storage at 50° C. after 24 hours, R241K exhibits better activity than WT. Activity was determined by the assay depicted in Scheme 1.

In order to determine the effects of sugar stabilizers, AOX variants were partially purified, freeze-dried in presence of 35 wt % stabilizer and incubated dry at 50° C. for the time period indicated. As shown in Table 2, particularly in the presence of a sugar stabilizer, the R241K variant exhibited improved stability compared to WT and an N218D variant.

TABLE 2

Residual activity of AOX at 50° C. in the presence of sugar stabilizers

| AOX | Stabilizer | 24 hr (%) | 4 days (%) | 4 weeks (%) |
|---|---|---|---|---|
| WT | none | 0 | 0 | 0 |
| R241K | none | 25 | 0 | 0 |
| WT | sucrose | 100 | 100 | 22 |
| WT | trehalose | 75 | 21 | 0 |
| N281D | sucrose | 80 | 67 | 10 |
| N281D | trehalose | 15 | 10 | 7 |
| R241K | sucrose | 100 | 100 | 25 |
| R241K | trehalose | 53 | 10 | 0 |

% = residual activity

The stability experiment was repeated for the R241K mutant after shaking flask growth and partial purification, freeze-drying in presence of stabilizer, and incubation with latex (70% stripped Rhoplex™) for time period indicated at RT in liquid. Specifically, lyophilized AOX-R241K was dissolved in 45% sucrose solution, then mixed in 1:4 volume per volume with stripped Rhoplex™, at 30° C. Residual activity was measured at regular intervals. The results are given in Table 3.

TABLE 3

Residual activity of AOX in latex binder at 50° C. in the presence of sugar stabilizers

| Sample | Stabilizer | 24 hr (%) | 48 hr (%) | 3 weeks (%) |
|---|---|---|---|---|
| WT | None | 0 | 0 | — |
| R241K | None | 25 | 13 | 0 |
| R241K | sucrose | 50 | 46 | 0 |

R241K is a variant that is more active and more stable than the WT AOX under the same growth and purification conditions. Carbohydrate stabilizers increase stability both at higher temperatures and in 80% latex, but not yet in combination. In the long term studies, 45% sucrose provides the best result.

Example 5

Preparation of Silica Support and Immobilized Enzymes

Mesocellular foam (MCF) silica was synthesized following a protocol known in the art. Pluronic® 123 (16 g) was dissolved in a solution of deionized water (260 g) and HCl (48 g) and, upon dissolution of P123, 1,3,5-trimethylbenzene (16 g) was added. The temperature of the solution was increased to 40° C. and stirred vigorously for 2 h. Tetraethyl orthosilicate (34.7 g) was added to the solution, stirred for an additional 5 min, and left quiescent at 40° C. overnight. A solution of $NH_4F$ (184 mg) in 20 mL of deionized water was added as a mineralization agent, stirred for five minutes, and left quiescent at 100° C. overnight. The resulting solid was filtered and washed with copious amounts of deionized water, followed by heating at 75° C. overnight and calcined in air at 550° C. with a ramp rate of $1.2° C.min^{-1}$.

FOX loading onto silica. MCF silica was weighed out in 50 mg portions in 1.7 mL microcentrifuge tubes until the desired total amount of silica was reached. FOX was loaded onto the silica support by first diluting with 0.1 M pH 7 potassium phosphate buffer until a concentration near 4 mg/mL was obtained. To each centrifuge tube, 1 mL of FOX solution was added and tubes were placed in a tube rotator (VWR) overnight. After taking off the rotator, all tubes were centrifuged and excess buffer solution was collected. The enzyme loaded silica was then redispersed in buffer solution, centrifuged, and the wash was collected. This process was repeated an additional two times.

A standard 2 mg/mL FOX solution was made, 1 mL total, for determining FOX loading using UV-Vis spectroscopy. Knowing the initial concentration of FOX when loading on to silica, the washes were diluted until a theoretical 2 mg/ml solution was obtained. UV-Vis analysis of the washes compared to the known 2 mg/ml concentration allowed for determination of enzyme loading. Activity assays, as previously mentioned for FOX, were conducted using a Hansatech Oxygraph equipped with the DW1 electrode chamber and S1 electrode to determine the initial rates of 02 consumption. Analysis solutions contained 980 μL of pH 4 0.1 M acetate buffer, 10 μL of 5 M sodium formate aqueous solution, and 10 μL of FOX solution (from the washes, standard, or silica slurry).

AOX loading onto silica. Similar to FOX, AOX was first diluted with 0.1 M pH 7 potassium phosphate buffer until a concentration near 8 mg/mL was obtained. Two centrifuge tubes were combined using 1 mL of AOX solution and the tubes were placed on the aforementioned tube rotator overnight. The enzyme-loaded silica was then washed and analyzed as previously mentioned with FOX. AOX active assays were conducted with solutions containing 980 μL of pH 7 0.1 M potassium phosphate buffer, 10 μL of 1M formaldehyde aqueous solution, and 10 μL of AOX solution (from the washes, standard, or silica slurry). The activity assay for FOX was again tested using the silica slurry to ensure that FOX remained immobilized and active after AOX loading.

Example 6

Preparation of Bioactive Coating and Detection of $^{13}C$ Labeled $CO_2$ from $^{13}C$ Labeled Formaldehyde Bioactive coatings (400 mg of AOX+FOD-loaded MCF silica suspended in 1 mL of 0.1 M potassium phosphate buffer, pH 7 prior to mixing with 1 mL of non-stripped Rhoplex™ acrylic binder spread out onto a surface until it is approximately 0.1 mm thick and allowed to dry) were enclosed in gas sampling bags (Tedlar 10 L, Restek Corp.). Th eenzyms were loaded onto bare MCF with no amines. Sampling bags were cut open to apply coatings and heat sealed. To prepare the bioactive coating, the desired amount of enzyme-loaded silica was mixed using 1 mL of 0.1 M pH 7 potassium phosphate buffer and 1 mL of Rhoplex™ acrylic binder. After mixing, 500 μL aliquots were spread along the inside of the sampling bag using a plastic applicator (Thomas Scientific) with a 0.1 mm thickness. Coatings were allowed to dry and two 0.65 mL microcentrifuge tubes, each filled with 30 of a 20% $^{13}C$ labeled formaldehyde solution in water (Cambridge Isotope) were added before completely heat sealing. Control bags were also prepared for analysis and included a sampling bag with only vials containing the $^{13}C$ formaldehyde solutions and a sampling bag with $^{13}C$ formaldehyde solutions and 1 mL of latex +1 mL of 0.1 M pH 7 potassium phosphate buffer (no enzyme-loaded silica).

After sample bags were sealed, they were transferred to a glovebox purged with humidified, $CO_2$ free air as to not interfere with sample analysis. Sample bags were purged multiple times with $CO_2$ free air and analyzed using an LI-840A IR gas analyzer (Li-Cor) to ensure $CO_2$ levels in the bags were below 5 ppm. Sample bags were then filled with 8 L of air using a gas sampling pump (Grab Air Sample Pump, SKC Inc.) and a mass flow meter (FMA1814, Omega Engineering Inc.) and vials of $^{13}C$ labeled formaldehyde solution were opened to reach an optimal 1,000 ppm.

After 24 h, sample bags were removed from the glovebox and analyzed via mass spectrometry (OmniStar™ gas analysis system, Pfeiffer Vacuum) using a gas sampling pump (Grab Air Sample Pump, SKC Inc.) to extract the gas content. Levels of $^{13}C$ labeled formaldehyde and $^{13}C$ labeled $CO_2$ were monitored after 24 and 48 h.

Figure 4:
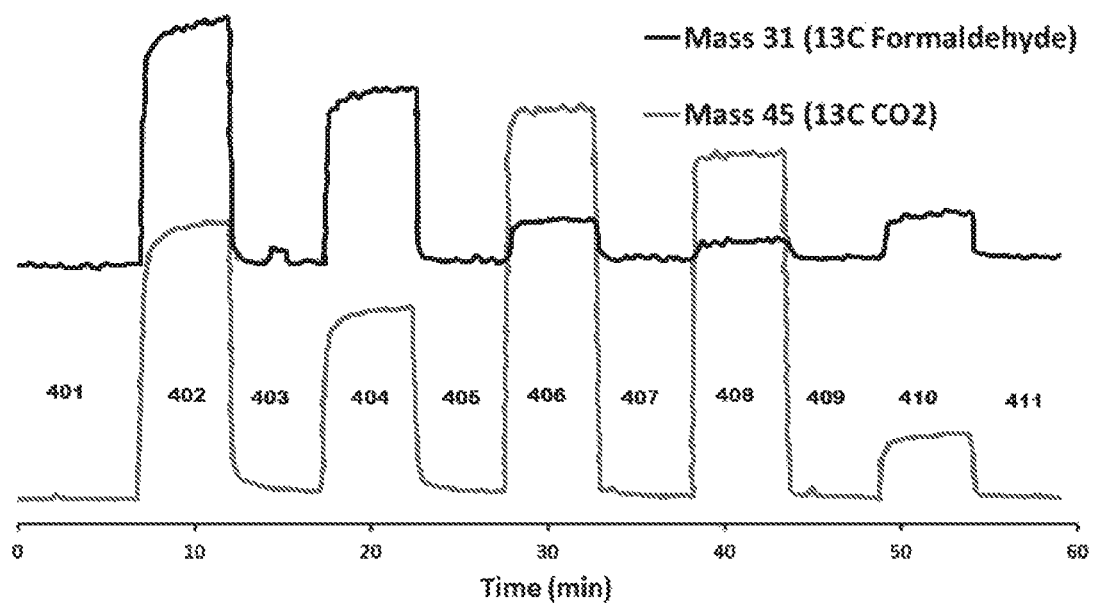
FIG. 4 shows the conversion of $^{13}C$ labeled formaldehyde to $^{13}C$ labeled $CO_2$ by AOX and FOX enzymes supported on mesostructured silica foam (MCF) silica particles, dispersed in a latex medium, and subsequently dried on a surface as a coating.

The mass spec results (FIG. 4) show conversion of $^{13}C$ labeled formaldehyde to $^{13}C$ labeled $CO_2$ by AOX and FOD enzymes supported on MCF silica particles, dispersed in a latex medium, and subsequently dried on a surface as a coating. Reference numbers 401, 403, 405, 407, 409, and 411 are all ambient conditions. 402 is $^{13}C$ formaldehyde, 404 is $^{13}C$ formaldehyde plus Rhoplex™, 406 is $^{13}C$ formaldehyde plus Rhoplex™ plus 200 mg MCF with AOX/FOD, 408 is $^{13}C$ formaldehyde plus Rhoplex™ plus 400 mg MCF with AOX/FOD, and 210 is $^{13}C$ formaldehyde plus Rhoplex™ plus free AOX/FOD, he mass 45 peak (labeled $CO_2$ peak; bottom trace) surpasses that of the controls while the mass 31 peak (labeled formaldehyde; top trace) decreased indicating conversion. The last test, free enzymes in latex, demonstrated that the MCF silica component is required for detectable conversion.

This disclosure is further illustrated by the following embodiments.

Embodiment 1. A coating for conversion of formaldehyde to carbon dioxide, the coating comprising: an alcohol/aldehyde oxidase and a formate oxidase, wherein both the alcohol/aldehyde oxidase and the formate oxidase are immobilized on a solid particulate support; and a latex binder.

Embodiment 2. The coating of embodiment 1, wherein the alcohol/aldehyde oxidase has greater than 95% sequence homology with an alcohol/aldehyde oxidase of SEQ ID NO: 1, specifically greater than 99% sequence homology with SEQ ID NO: 1.

Embodiment 3. The coating of embodiment 1, wherein the alcohol/aldehyde oxidase is of SEQ ID NO: 1 having a R241K mutation or a N218D mutation.

Embodiment 4. The coating of embodiment 1, wherein the formate oxidase has SEQ ID NO: 2.

Embodiment 5. The coating of any one or more of embodiments 1 to 4, wherein the olid particulate support is an inorganic support, preferably a porous inorganic support.

Embodiment 6. The coating of embodiment 5, wherein the inorganic particulate support has a particle diameter of 0.1 to 800 micrometers, preferably 0.5 to 100 micrometers, and a pore diameter of 50 Angstroms to 200 nanometers, preferably 100 Angstroms to 50 nanometers.

Embodiment 7. The coating of any one or more of embodiments 1 to 6, wherein the solid particulate support comprises silica, preferably wherein the silica is a mesocellular foam, porous micro spheres, porous core-shell particles, porous nanoparticles, particles with a porous silica layer, or a combination comprising at least one of the foregoing.

Embodiment 8. The coating of any one or more of embodiments 1 to 7, wherein the latex binder is an acrylic latex, an acrylonitrile-butadiene latex, an alkyd latex, an ethylene-vinyl acetate latex, a natural rubber latex, a neoprene latex, a polyamide latex, a polybutadiene latex, a polybutylene latex, a polychloroprene latex, a polyester latex, a polyisoprene latex, a polypropylene latex, a polyurethane latex, a polyvinyl alcohol latex, a polyvinyl butyral latex, a polyvinyl chloride latex, a polyvinylidene chloride latex, a silicone emulsion latex, a styrene-acrylic latex, a styrene-acrylonitrile latex, a styrene-butadiene rubber latex, a styrene-isoprene latex, a vinyl acetate latex, vinyl-acryl latex or a combination comprising at least one of the foregoing, preferably wherein the latex binder comprises an acrylic latex, a styrene-acrylic latex, a vinyl acetate latex, or a combination comprising at least one of the foregoing.

Embodiment 9. The coating of any one or more of embodiment 1 to 8, wherein the coating further comprises an enzyme stabilizer, a plasticizer, a rheology modifier, a thickener, a film forming agent, a surfactant, a preservative, a biocide, a mildewcide, a colorant, a defoaming agent, a dispersing agent, a drying retarder, an extending agent, a pH adjuster, a wax, or a combination comprising at least one of the foregoing.

Embodiment 10. The coating of any one or more of embodiments 1 to 9, wherein the enzyme stabilizer comprises a monosaccharide, a disaccharide, or an oligosaccharide containing 3 to 10 monosaccharide units, preferably wherein the enzyme stabilizer is include sucrose, trehalose, mannitol, sorbitol, xylose, xylitol, mannose, raffinose, lactose, maltose, galactose, or a combination comprising at least one of the foregoing, more preferably wherein the enzyme stabilizer is a sucrose, a trehalose, a mannitol, a sorbitol, or a combination comprising at least one of the foregoing.

Embodiment 11. The coating of any one or more of embodiments 1 to 10, wherein the coating is a paint for a building interior.

Embodiment 12. The coating of any one or more of embodiments 1 to 11, wherein the coating has a color difference quantified by CIELAB metric DE of less than 5, preferably less than 2 as measured by ASTM D2244 compared to a non-enzyme containing control.

Embodiment 13. The coating of any one or more of embodiments 1 to 12, where formaldehyde is abated in the air with an abatement efficiency as defined by at least 75% removal of starting levels of formaldehyde in the air as determined spectrophotometrically by Test method JC/T 1074-2008.

Embodiment 14. A liquid coating composition for the formation of the coating of any one or more of embodiments 1 to 13, comprising: an aldehyde oxidase and a formate oxidase immobilized on a solid particulate support; and a liquid latex binder composition.

Embodiment 15. A method for forming a coating, the method comprising: coating the liquid coating composition of embodiment 14 onto a substrate; and drying the liquid coating composition to form the coating.

Embodiment 16. A method for converting atmospheric formaldehyde to carbon dioxide, the method comprising: contacting the coating of any one or more of embodiments 1 to 13 with an atmosphere comprising formaldehyde; and converting at least a portion of the formaldehyde to carbon dioxide.

Embodiment 17. The method of embodiment 16, wherein the atmosphere is in a building interior.

Embodiment 18. An alcohol/aldehyde oxidase is of SEQ ID NO: 1 having a R241K mutation or a N218D mutation.

The compositions, methods, and articles can alternatively comprise, consist of, or consist essentially of, any appropriate components or steps herein disclosed. The compositions, methods, and articles can additionally, or alternatively, be formulated so as to be devoid, or substantially free, of any steps, components, materials, ingredients, adjuvants, or species that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to denote one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise.

Unless defined otherwise, technical and scientific terms used herein have the same meaning as is commonly understood by one of skill in the art to which this invention belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

---

What is claimed is:

1. A coating for conversion of formaldehyde to carbon dioxide, the coating comprising:
   an alcohol/aldehyde oxidase and a formate oxidase, wherein both the alcohol/aldehyde oxidase and the formate oxidase are immobilized on a solid particulate support; and
   a latex binder,
   wherein the alcohol/aldehyde oxidase
   a) has greater than 95% sequence homology with the amino acid sequence of SEQ ID NO: 1, or polypeptide of SEQ ID NO: 1 with a R241K mutation or a N218D, or
   b) is the polypeptide of SEQ ID NO: 1 with a R241K mutation or a N218D mutation.

2. The coating of claim 1, wherein the solid particulate support is an inorganic support.

3. The coating of claim 2, wherein the inorganic particulate support has a particle diameter of 0.1 to 800 micrometers.

4. The coating of claim 1, wherein the solid particulate support comprises silica.

5. The coating of claim 1, wherein the latex binder is an acrylic latex, an acrylonitrile-butadiene latex, an alkyd latex, an ethylene-vinyl acetate latex, a natural rubber latex, a neoprene latex, a polyamide latex, a polybutadiene latex, a polybutylene latex, a polychloroprene latex, a polyester latex, a polyisoprene latex, a polypropylene latex, a polyurethane latex, a polyvinyl alcohol latex, a polyvinyl butyral latex, a polyvinyl chloride latex, a polyvinylidene chloride latex, a silicone emulsion latex, a styrene-acrylic latex, a styrene-acrylonitrile latex, a styrene-butadiene rubber latex, a styrene-isoprene latex, a vinyl acetate latex, vinyl-acryl latex or a combination comprising at least one of the foregoing.

6. The coating of claim 1, wherein the coating further comprises an enzyme stabilizer, a plasticizer, a rheology modifier, a thickener, a film forming agent, a surfactant, a preservative, a biocide, a mildewcide, a colorant, a defoaming agent, a dispersing agent, a drying retarder, an extending agent, a pH adjuster, a wax, or a combination comprising at least one of the foregoing.

7. The coating of claim 1, wherein the enzyme stabilizer comprises a monosaccharide, a disaccharide, or an oligosaccharide containing 3 to 10 monosaccharide units.

8. The coating of claim 1, wherein the coating is a paint for a building interior.

9. The coating of claim 1, wherein the coating has a color difference quantified by CIELAB metric DE of less than 5 compared to a non-enzyme containing control.

10. The coating of claim 1, where formaldehyde is abated in the air with an abatement efficiency as defined by at least 75% removal of starting levels of formaldehyde in the air as determined spectrophotometrically by Test method JC/T 1074-2008.

11. The coating of claim 1, where the formate oxidase has the amino acid sequence of SEQ ID NO: 2.

12. A liquid coating composition for the formation of the coating of claim 1, comprising:
   an alcohol/aldehyde oxidase and a formate oxidase, wherein both the aldehyde oxidase and the formate oxidase are immobilized on a solid particulate support;
   wherein the alcohol/aldehyde oxidase
   a) has greater than 95% sequence homology with the amino acid sequence of SEQ ID NO: 1, or
   b) is the polypeptide of SEQ ID NO: 1 with a R241K mutation or a N218D mutation; and
   a liquid latex binder composition.

13. A method for forming a coating, the method comprising:
   coating the liquid coating composition of claim 12 onto a substrate; and
   drying the liquid coating composition to form the coating.

14. A method for converting atmospheric formaldehyde to carbon dioxide, the method comprising:
   contacting the coating of claim 1 with an atmosphere comprising formaldehyde; and
   converting at least a portion of the formaldehyde to carbon dioxide.

15. The method of claim 14, wherein the atmosphere is in a building interior.

16. An alcohol/aldehyde oxidase with the amino acid sequence of SEQ ID NO: 1 wherein said sequence has a R241K mutation or a N218D mutation.

* * * * *

SEQUENCE LISTING

```
<160> NUMBER OF SEQ ID NOS: 5

<210> SEQ ID NO 1
<211> LENGTH: 663
<212> TYPE: PRT
<213> ORGANISM: Pichia pastoris

<400> SEQUENCE: 1
```

Met Ala Ile Pro Glu Glu Phe Asp Ile Leu Val Leu Gly Gly Gly Ser
1               5                   10                  15

Ser Gly Ser Cys Ile Ala Gly Arg Leu Ala Asn Leu Asp His Ser Leu
            20                  25                  30

Lys Val Gly Leu Ile Glu Ala Gly Glu Asn Asn Leu Asn Asn Pro Trp
        35                  40                  45

Val Tyr Leu Pro Gly Ile Tyr Pro Arg Asn Met Lys Leu Asp Ser Lys
    50                  55                  60

Thr Ala Ser Phe Tyr Thr Ser Asn Pro Ser Pro His Leu Asn Gly Arg
65                  70                  75                  80

Arg Ala Ile Val Pro Cys Ala Asn Val Leu Gly Gly Gly Ser Ser Ile
                85                  90                  95

Asn Phe Met Met Tyr Thr Arg Gly Ser Ala Ser Asp Tyr Asp Asp Phe
            100                 105                 110

```
Gln Ala Glu Gly Trp Lys Thr Lys Asp Leu Leu Pro Leu Met Lys Lys
            115                 120                 125

Thr Glu Thr Tyr Gln Arg Ala Cys Asn Pro Asp Ile His Gly Phe
    130                 135                 140

Glu Gly Pro Ile Lys Val Ser Phe Gly Asn Tyr Thr Tyr Pro Val Cys
145                 150                 155                 160

Gln Asp Phe Leu Arg Ala Ser Glu Ser Gln Gly Ile Pro Tyr Val Asp
                165                 170                 175

Asp Leu Glu Asp Leu Val Thr Ala His Gly Ala Glu His Trp Leu Lys
            180                 185                 190

Trp Ile Asn Arg Asp Thr Gly Arg Arg Ser Asp Ser Ala His Ala Phe
        195                 200                 205

Val His Ser Thr Met Arg Asn His Asp Asn Leu Tyr Leu Ile Cys Asn
    210                 215                 220

Thr Lys Val Asp Lys Ile Ile Val Glu Asp Gly Arg Ala Ala Ala Val
225                 230                 235                 240

Arg Thr Val Pro Ser Lys Pro Leu Asn Pro Lys Lys Pro Ser His Lys
                245                 250                 255

Ile Tyr Arg Ala Arg Lys Gln Ile Val Leu Ser Cys Gly Thr Ile Ser
            260                 265                 270

Ser Pro Leu Val Leu Gln Arg Ser Gly Phe Gly Asp Pro Ile Lys Leu
        275                 280                 285

Arg Ala Ala Gly Val Lys Pro Leu Val Asn Leu Pro Gly Val Gly Arg
    290                 295                 300

Asn Phe Gln Asp His Tyr Cys Phe Phe Ser Pro Tyr Arg Ile Lys Pro
305                 310                 315                 320

Gln Tyr Glu Ser Phe Asp Asp Phe Val Arg Gly Asp Ala Glu Ile Gln
                325                 330                 335

Lys Arg Val Phe Asp Gln Trp Tyr Ala Asn Gly Thr Gly Pro Leu Ala
            340                 345                 350

Thr Asn Gly Ile Glu Ala Gly Val Lys Ile Arg Pro Thr Pro Glu Glu
        355                 360                 365

Leu Ser Gln Met Asp Glu Ser Phe Gln Glu Gly Tyr Arg Glu Tyr Phe
    370                 375                 380

Glu Asp Lys Pro Asp Lys Pro Val Met His Tyr Ser Ile Ile Ala Gly
385                 390                 395                 400

Phe Phe Gly Asp His Thr Lys Ile Pro Pro Gly Lys Tyr Met Thr Met
                405                 410                 415

Phe His Phe Leu Glu Tyr Pro Phe Ser Arg Gly Ser Ile His Ile Thr
            420                 425                 430

Ser Pro Asp Pro Tyr Ala Ala Pro Asp Phe Asp Pro Gly Phe Met Asn
        435                 440                 445

Asp Glu Arg Asp Met Ala Pro Met Val Trp Ala Tyr Lys Lys Ser Arg
    450                 455                 460

Glu Thr Ala Arg Arg Met Asp His Phe Ala Gly Glu Val Thr Ser His
465                 470                 475                 480

His Pro Leu Phe Pro Tyr Ser Ser Glu Ala Arg Ala Leu Glu Met Asp
                485                 490                 495

Leu Glu Thr Ser Asn Ala Tyr Gly Gly Pro Leu Asn Leu Ser Ala Gly
            500                 505                 510

Leu Ala His Gly Ser Trp Thr Gln Pro Leu Lys Lys Pro Thr Ala Lys
        515                 520                 525
```

```
Asn Glu Gly His Val Thr Ser Asn Gln Val Glu Leu His Pro Asp Ile
    530                 535                 540

Glu Tyr Asp Glu Glu Asp Lys Ala Ile Glu Asn Tyr Ile Arg Glu
545                 550                 555                 560

His Thr Glu Thr Thr Trp His Cys Leu Gly Thr Cys Ser Ile Gly Pro
                    565                 570                 575

Arg Glu Gly Ser Lys Ile Val Lys Trp Gly Val Leu Asp His Arg
                580                 585                 590

Ser Asn Val Tyr Gly Val Lys Gly Leu Lys Val Gly Asp Leu Ser Val
                595                 600                 605

Cys Pro Asp Asn Val Gly Cys Asn Thr Tyr Thr Ala Leu Leu Ile
610                 615                 620

Gly Glu Lys Thr Ala Thr Leu Val Gly Glu Asp Leu Gly Tyr Ser Gly
625                 630                 635                 640

Glu Ala Leu Asp Met Thr Val Pro Gln Phe Lys Leu Gly Thr Tyr Glu
                645                 650                 655

Lys Thr Gly Leu Ala Arg Phe
                660

<210> SEQ ID NO 2
<211> LENGTH: 578
<212> TYPE: PRT
<213> ORGANISM: Aspergillus oryzae

<400> SEQUENCE: 2

Met Ala Thr Asp Gly Ser His Phe Asp Phe Val Ile Val Gly Gly Gly
1               5                   10                  15

Thr Ala Gly Asn Thr Val Ala Gly Arg Leu Ala Glu Asn Pro Asn Val
                20                  25                  30

Thr Val Leu Ile Val Glu Ala Gly Ile Gly Asn Pro Glu Asp Ile Pro
            35                  40                  45

Glu Ile Thr Thr Pro Ser Ser Ala Met Asp Leu Arg Asn Ser Lys Tyr
        50                  55                  60

Asp Trp Ala Tyr Lys Thr Thr Met Val Arg Arg Asp Asp Tyr Glu Arg
65                  70                  75                  80

Ile Glu Lys Pro Asn Thr Arg Gly Lys Thr Leu Gly Gly Ser Ser Ser
                85                  90                  95

Leu Asn Tyr Phe Thr Trp Val Pro Gly His Lys Ala Thr Phe Asp Gln
                100                 105                 110

Trp Glu Glu Phe Gly Gly Lys Glu Trp Thr Trp Asp Pro Leu Val Pro
            115                 120                 125

Tyr Leu Arg Lys Ser Ala Thr Tyr His Asp Asp Pro Arg Leu Tyr Ser
        130                 135                 140

Pro Glu Leu Glu Lys Ile Gly Gly Gly Pro Ile Pro Ile Ser His
145                 150                 155                 160

Ala Glu Leu Ile Asp Glu Met Ala Pro Phe Arg Glu Asn Leu Thr Lys
                165                 170                 175

Ala Trp Lys Ser Met Gly Gln Pro Leu Ile Glu Asn Ile Tyr Asp Gly
                180                 185                 190

Glu Met Asp Gly Leu Thr His Cys Cys Asp Thr Ile Tyr Arg Gly Gln
            195                 200                 205

Arg Ser Gly Ser Phe Leu Phe Val Lys Asn Lys Pro Asn Ile Thr Ile
        210                 215                 220

Val Pro Glu Val His Ser Lys Arg Leu Ile Ile Asn Glu Ala Asp Arg
225                 230                 235                 240
```

```
Thr Cys Lys Gly Val Thr Val Thr Ala Ala Gly Asn Glu Leu Asn
            245             250                 255

Phe Phe Ala Asp Arg Glu Val Ile Leu Ser Gln Gly Val Phe Glu Thr
            260                 265                 270

Pro Lys Leu Leu Met Leu Ser Gly Ile Gly Pro Thr Arg Glu Leu Ser
            275                 280                 285

Arg His Gly Ile Asn Thr Ile Val Asp Ser Arg His Val Gly Gln Asn
            290                 295                 300

Leu Met Asp His Pro Gly Val Pro Phe Val Leu Arg Val Lys Asp Gly
305                 310                 315                 320

Phe Gly Met Asp Asp Val Leu Leu Arg His Gly Pro Lys Arg Asp Ala
                325                 330                 335

Val Val Ser Ala Tyr Asn Lys Asn Arg Ser Gly Pro Val Gly Ser Gly
            340                 345                 350

Leu Leu Glu Leu Val Gly Phe Pro Arg Ile Asp Lys Tyr Leu Glu Lys
            355                 360                 365

Asp Ala Glu Tyr Arg Lys Ala Lys Ala Ala Asn Gly Gly Lys Asp Pro
            370                 375                 380

Phe Ser Pro Leu Gly Gln Pro His Phe Glu Leu Asp Phe Val Cys Met
385                 390                 395                 400

Phe Gly Thr Ala Phe Gln Trp His Phe Pro Thr Pro Lys Thr Gly Asp
                405                 410                 415

His Leu Thr Val Val Asp Leu Val Arg Pro Ile Ser Asp Pro Gly
            420                 425                 430

Glu Val Thr Leu Asn Ser Ala Asp Pro Phe Gln Gln Pro Asn Ile Asn
            435                 440                 445

Leu Asn Phe Phe Ala Asn Asp Leu Asp Ile Ile Ala Met Arg Glu Gly
            450                 455                 460

Ile Arg Phe Ser Tyr Asp Leu Leu Phe Lys Gly Glu Gly Phe Lys Asp
465                 470                 475                 480

Leu Val Glu Ser Glu Tyr Pro Trp Glu Met Pro Leu Asp Ser Asp Lys
                485                 490                 495

Glu Met His Arg Ala Val Leu Asp Arg Cys Gln Thr Ala Phe His Pro
            500                 505                 510

Thr Gly Thr Ala Arg Leu Ser Lys Asn Ile Asp Gln Gly Val Val Asp
            515                 520                 525

Pro Lys Leu Lys Val His Gly Ile Lys Lys Leu Arg Val Ala Asp Ala
            530                 535                 540

Ser Val Ile Pro Ile Ile Pro Asp Cys Arg Ile Gln Asn Ser Val Tyr
545                 550                 555                 560

Ala Val Gly Glu Lys Cys Ala Asp Met Ile Lys Ala Glu His Lys Asp
                565                 570                 575

Leu Tyr

<210> SEQ ID NO 3
<211> LENGTH: 1734
<212> TYPE: DNA
<213> ORGANISM: Aspergillus oryzae

<400> SEQUENCE: 3
atggcaaccg atggtagcca ttttgatttt gttattgttg gtggtggcac cgcaggtaat      60
accgttgcag tcgtctggc agaaaatccg aatgttaccg ttctgattgt tgaagccggt     120
attggtaatc cggaagatat cccggaaatt accaccccga gcagcgcaat ggatctgcgt     180
```

| | |
|---|---|
| aatagcaaat atgattgggc ctataaaacc accatggttc gtcgtgatga ttatgaacgt | 240 |
| attgaaaaac cgaatacccg tggtaaaacc ctgggtggta gcagcagcct gaactatttt | 300 |
| acctgggttc cgggtcataa agcaacctt gatcagtggg aagaatttgg tggtaaagaa | 360 |
| tggacctggg atccgctggt tccgtatctg cgcaaaagcg caacctatca tgatgatccg | 420 |
| cgtctgtata gtccggaact ggaaaaaatt ggtggcggtg gtccgattcc gattagccat | 480 |
| gcagaactga ttgatgaaat ggcaccgttt cgtgaaaatc tgaccaaagc atggaaaagc | 540 |
| atgggtcagc cgctgattga aacatttat gatggtgaaa tggatggcct gacccattgt | 600 |
| tgtgatacca tttatcgtgg tcagcgtagc ggtagctttc tgtttgttaa aaacaaaccg | 660 |
| aacattacca ttgtgccgga agttcatagc aaacgcctga ttattaacga agcagatcgt | 720 |
| acctgtaaag gtgttaccgt ggttaccgca gcaggtaatg aactgaactt ttttgcagat | 780 |
| cgtgaagtga ttctgagcca gggtgttttt gaaaccccga actgctgat gctgagtggt | 840 |
| attggtccga cccgtgaact gagccgtcat ggcattaata ccattgttga tagtcgtcat | 900 |
| gttggccaga atctgatgga tcatccgggt gttccgtttg ttctgcgtgt taaagatggt | 960 |
| tttggtatgg atgatgttct gctgcgtcat ggtccgaaac gtgatgcagt tgttagcgca | 1020 |
| tataacaaaa atcgtagcgg tccggttggt agcggtctgc tggaactggt tggttttccg | 1080 |
| cgtattgata aatacctgga aaaagatgcc gaatatcgta agcaaaagc agcaaatggt | 1140 |
| ggcaaagatc cgtttagtcc gctgggccag ccgcattttg aactggatt tgtttgtatg | 1200 |
| tttggcaccg cctttcagtg gcattttccg accccgaaaa ccggtgatca tctgaccgtt | 1260 |
| gttgttgatc tggttcgtcc gattagtgat ccgggtgaag ttaccctgaa tagtgccgat | 1320 |
| ccgtttcagc agccgaatat taacctgaat tttttcgcca acgatctgga cattattgca | 1380 |
| atgcgtgaag gtattcgctt tagctatgat ctgctgttta aggcgaagg ctttaaagat | 1440 |
| ctggttgaaa gtgaatatcc gtgggaaatg ccgctggata gcgataaaga aatgcatcgt | 1500 |
| gcagttctgg atcgttgtca gaccgcattt catccgaccg gcaccgcacg tctgagcaaa | 1560 |
| aacattgatc agggtgttgt ggatccgaaa ctgaaagttc atggtatcaa aaaactgcgt | 1620 |
| gttgcagatg caagcgttat tccgatcatt ccggattgtc gtattcagaa tagcgtttat | 1680 |
| gcagtgggtg aaaaatgtgc cgatatgatt aaagccgaac acaaagacct gtat | 1734 |

```
<210> SEQ ID NO 4
<211> LENGTH: 33
<212> TYPE: DNA
<213> ORGANISM: artificial
<220> FEATURE:
<223> OTHER INFORMATION: comment primer

<400> SEQUENCE: 4
```

| | |
|---|---|
| cacaaagacc tgtattaagc cgcactggag cac | 33 |

```
<210> SEQ ID NO 5
<211> LENGTH: 33
<212> TYPE: DNA
<213> ORGANISM: artificial
<220> FEATURE:
<223> OTHER INFORMATION: comment primer

<400> SEQUENCE: 5
```

| | |
|---|---|
| gtgctcgagt gcggcttaat acaggtcttt gtg | 33 |